United States Patent
Li et al.

(10) Patent No.: US 8,541,217 B2
(45) Date of Patent: Sep. 24, 2013

(54) CYTOBLOCK PREPARATION SYSTEM AND METHODS OF USE

(75) Inventors: Rongshan Li, Basking Ridge, NJ (US); Wu Li, San Lorenzo, CA (US)

(73) Assignee: Rongshan Li, Basking Ridge, NJ (US)

(*) Notice: Subject to any disclaimer, the term of this patent is extended or adjusted under 35 U.S.C. 154(b) by 0 days.

(21) Appl. No.: 13/439,559

(22) Filed: Apr. 4, 2012

(65) Prior Publication Data
US 2012/0196344 A1  Aug. 2, 2012

Related U.S. Application Data

(63) Continuation of application No. 11/688,276, filed on Mar. 20, 2007, now Pat. No. 8,152,738.

(60) Provisional application No. 60/852,798, filed on Oct. 19, 2006, provisional application No. 60/846,036, filed on Sep. 20, 2006, provisional application No. 60/801,759, filed on May 20, 2006, provisional application No. 60/783,881, filed on Mar. 20, 2006.

(51) Int. Cl.
*C12N 11/00* (2006.01)

(52) U.S. Cl.
USPC .......... 435/174; 435/283.1; 435/297.2; 435/308.1; 600/564; 600/566; 600/567; 604/406; 604/239; 606/167

(58) Field of Classification Search
None
See application file for complete search history.

(56) References Cited

U.S. PATENT DOCUMENTS

| | | | |
|---|---|---|---|
| 5,137,710 A | | 8/1992 | Smalley et al. |
| 5,301,685 A | | 4/1994 | Guirguis |
| 5,427,742 A | * | 6/1995 | Holland ............... 422/536 |
| 5,645,537 A | | 7/1997 | Powles et al. |
| 5,649,911 A | | 7/1997 | Trerotola |
| 5,817,032 A | * | 10/1998 | Williamson et al. ....... 600/562 |
| 5,902,279 A | | 5/1999 | Powles et al. |
| 6,406,840 B1 | * | 6/2002 | Li et al. ............... 435/1.3 |
| 6,465,242 B1 | | 10/2002 | Kanipayor et al. |
| 2004/0121456 A1 | | 6/2004 | Fischer |
| 2005/0101879 A1 | | 5/2005 | Shidham et al. |
| 2005/0113715 A1 | | 5/2005 | Schwindt et al. |

FOREIGN PATENT DOCUMENTS

WO   84/04068   10/1984

OTHER PUBLICATIONS

International Search Report and Written Opinion for International Application No. PCT/US2007/064343 mailed Nov. 19, 2008.

\* cited by examiner

*Primary Examiner* — Dirk Bass
(74) *Attorney, Agent, or Firm* — Graham Curtin, P.A.

(57) ABSTRACT

An apparatus and method that may be used for collecting target cells or tissue and preparing a cell block are disclosed.

14 Claims, 35 Drawing Sheets

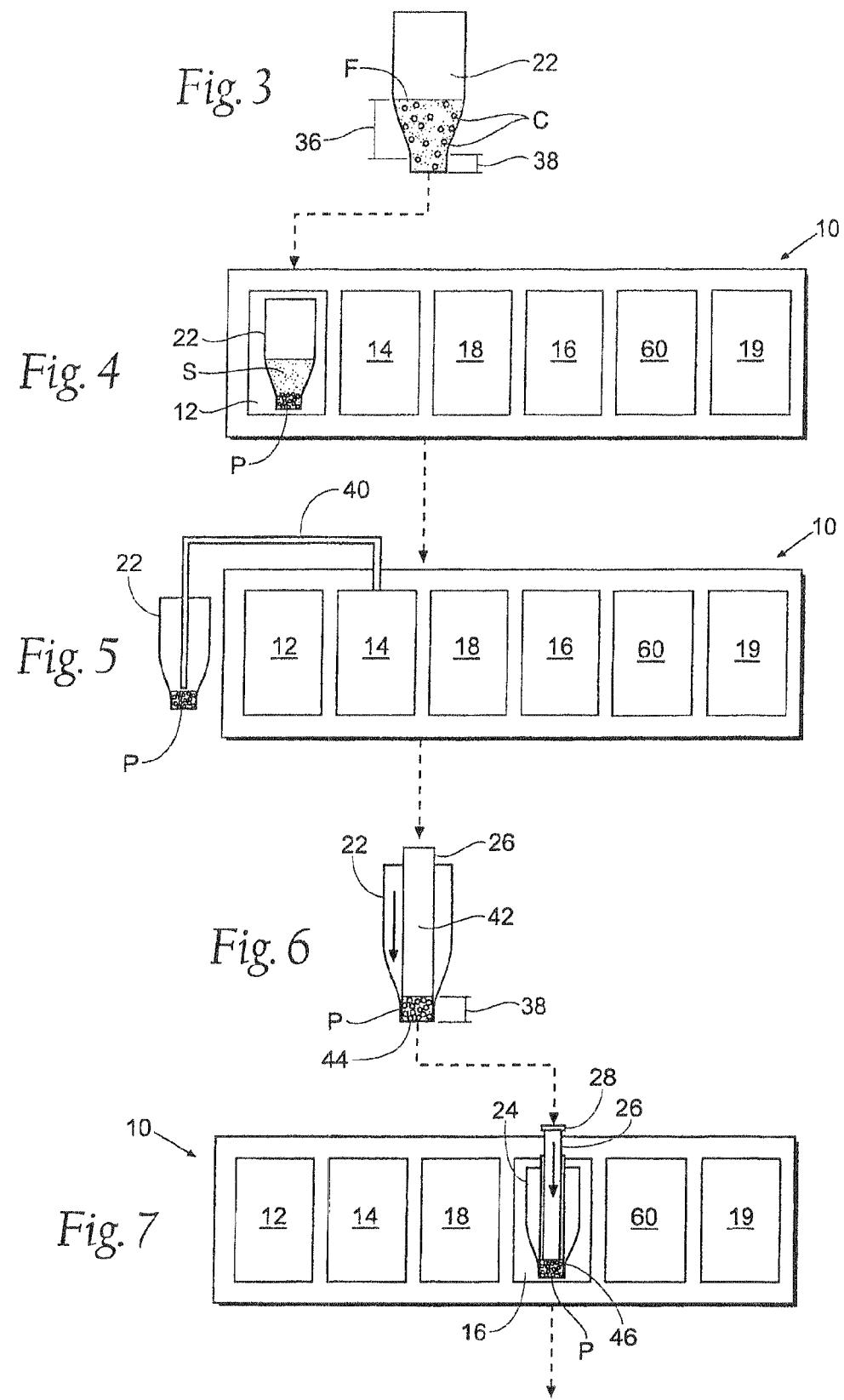

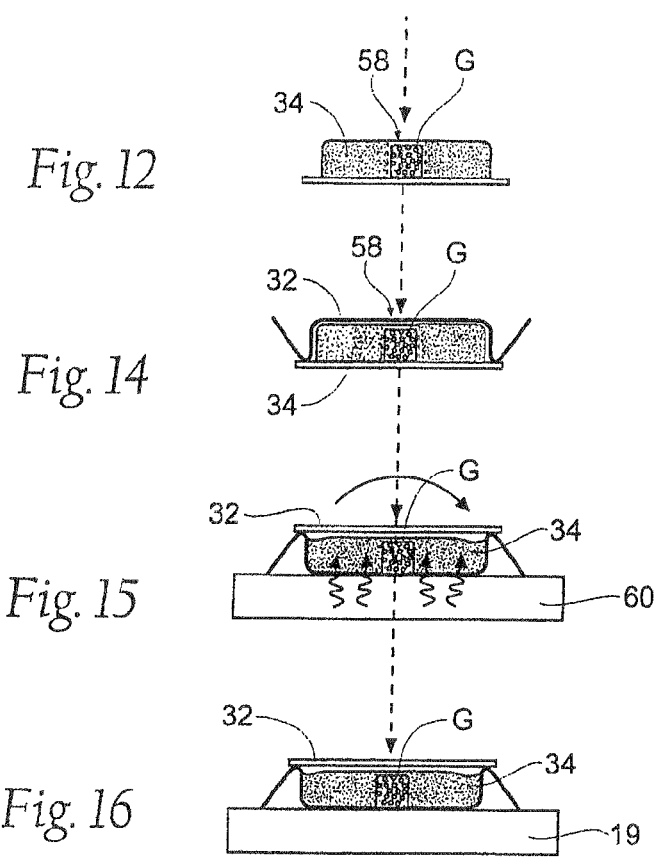
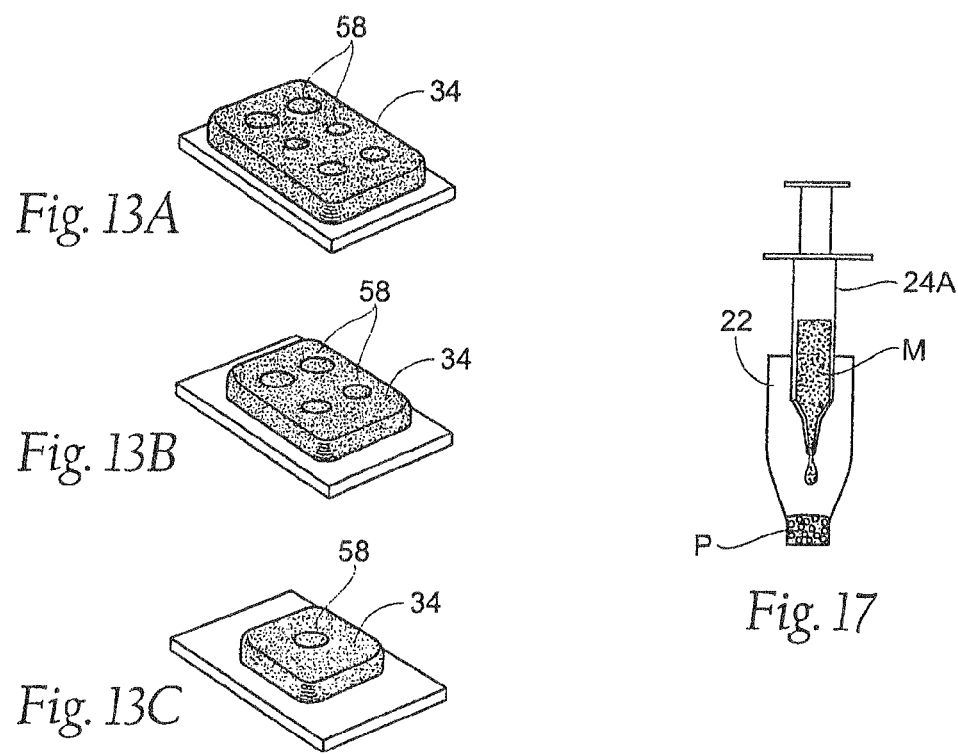

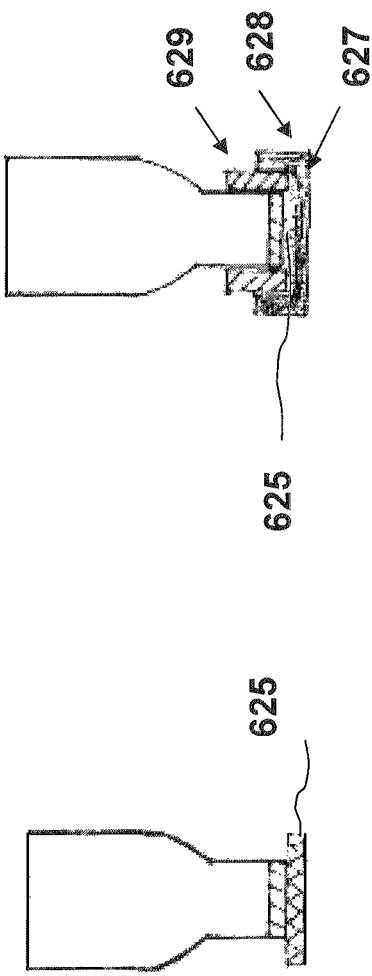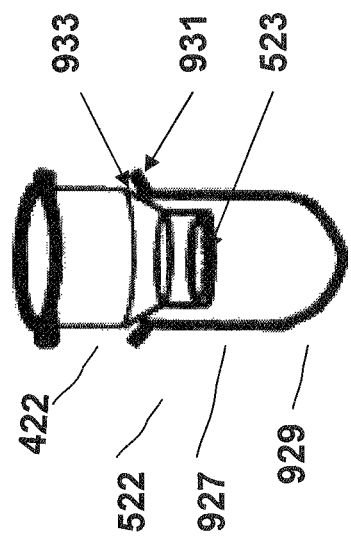

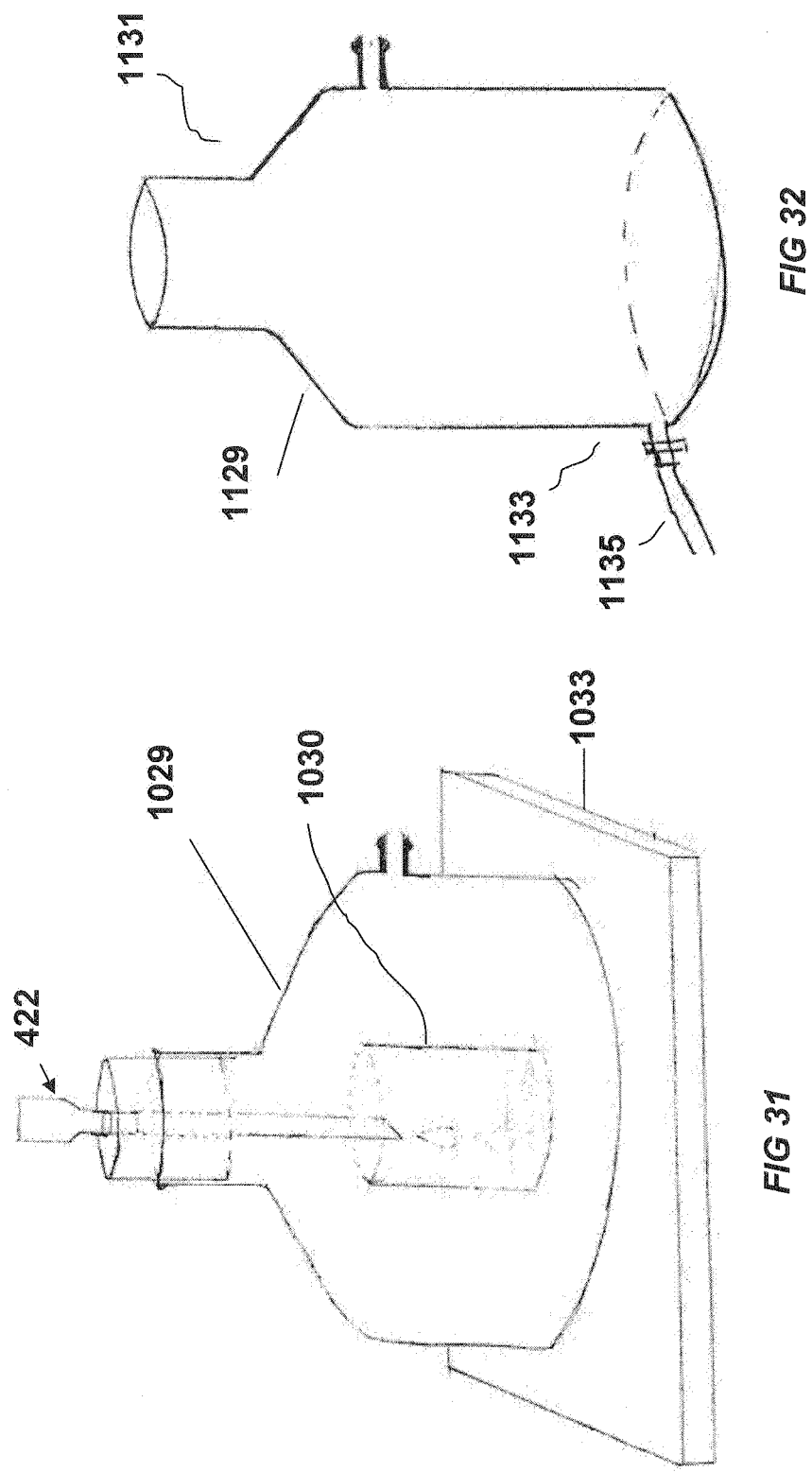

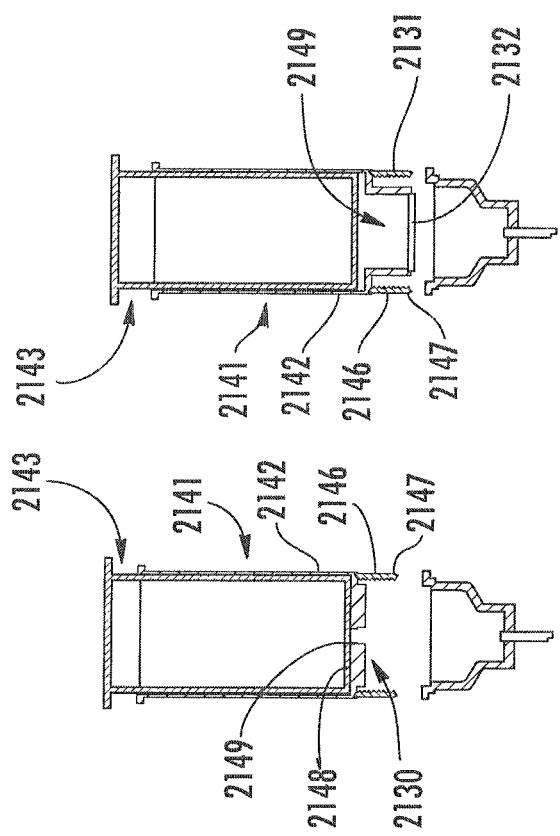

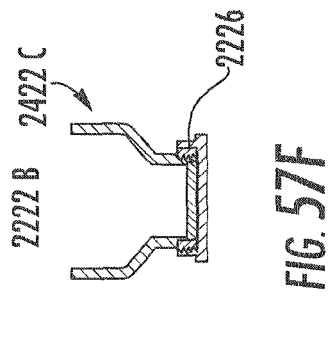
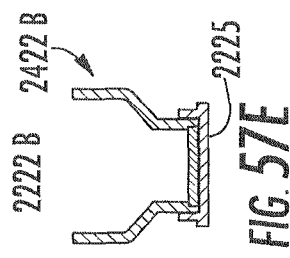
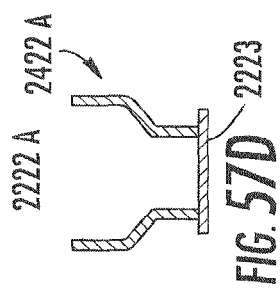
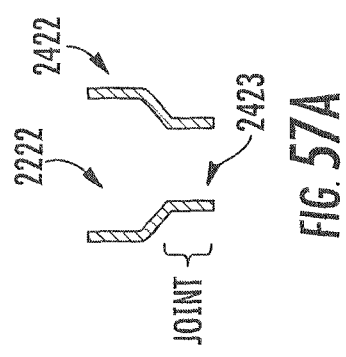
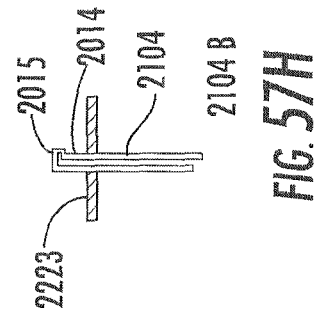
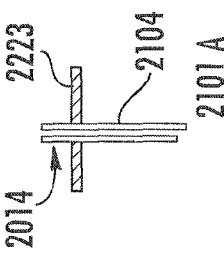
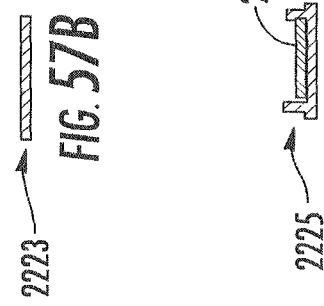

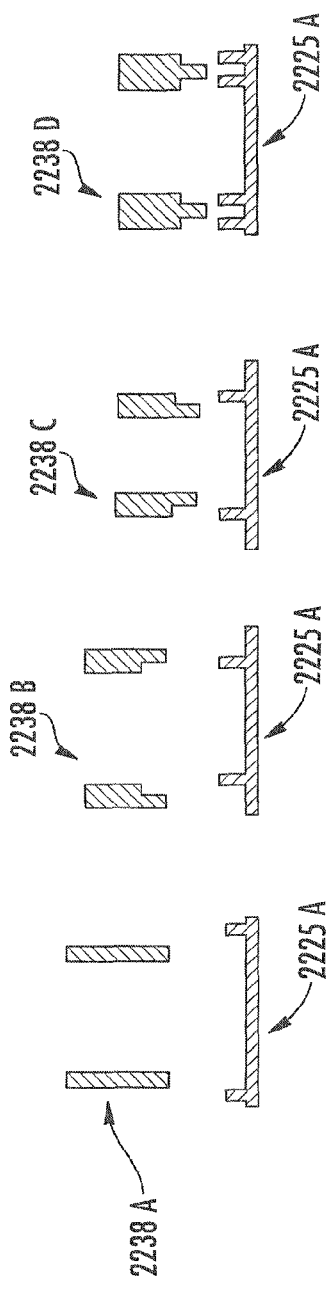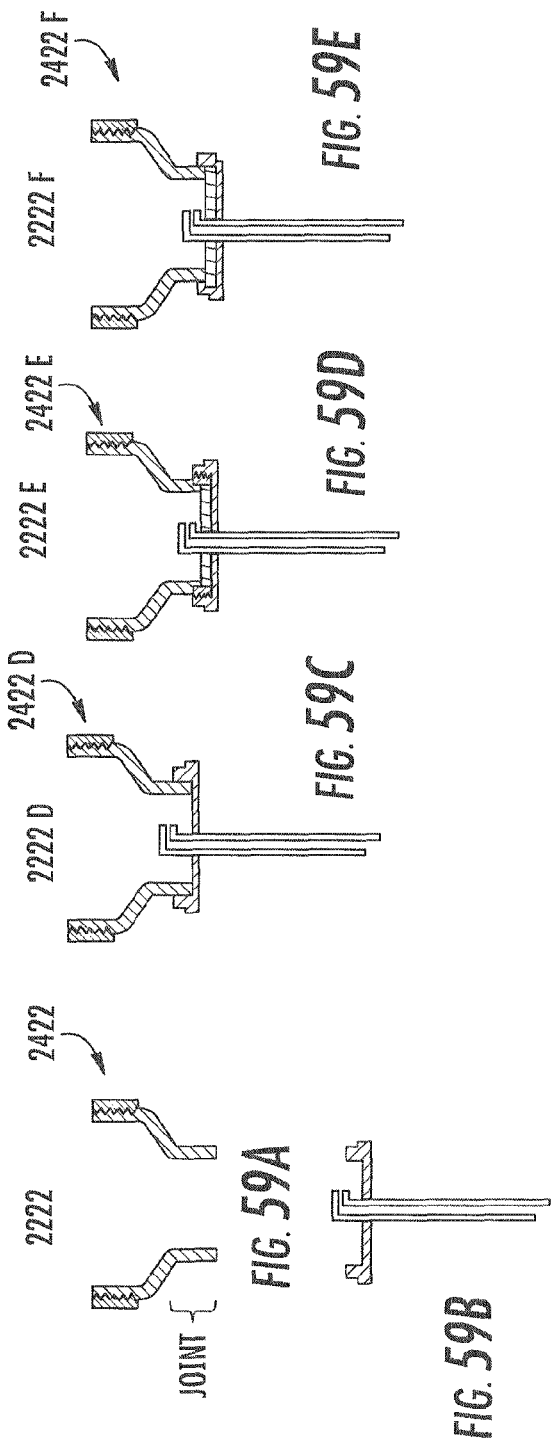

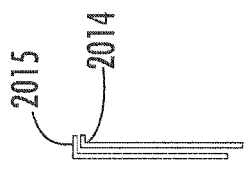
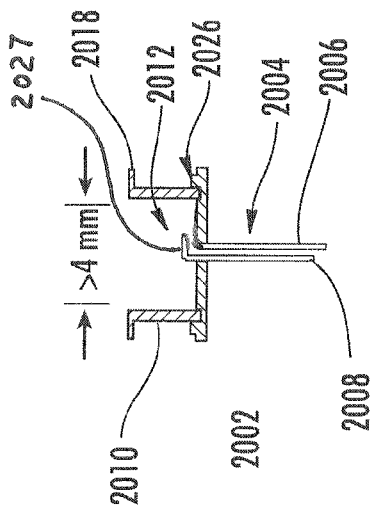
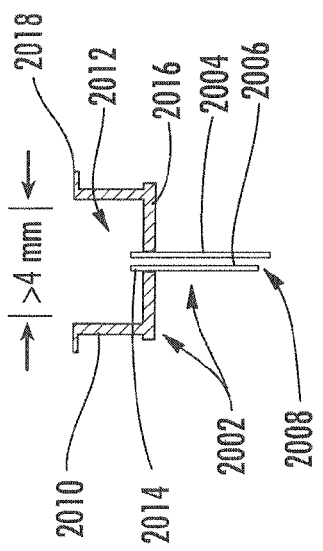
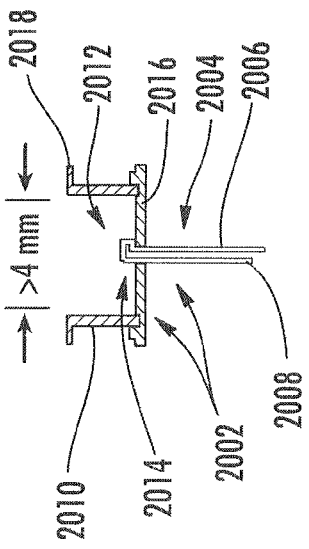

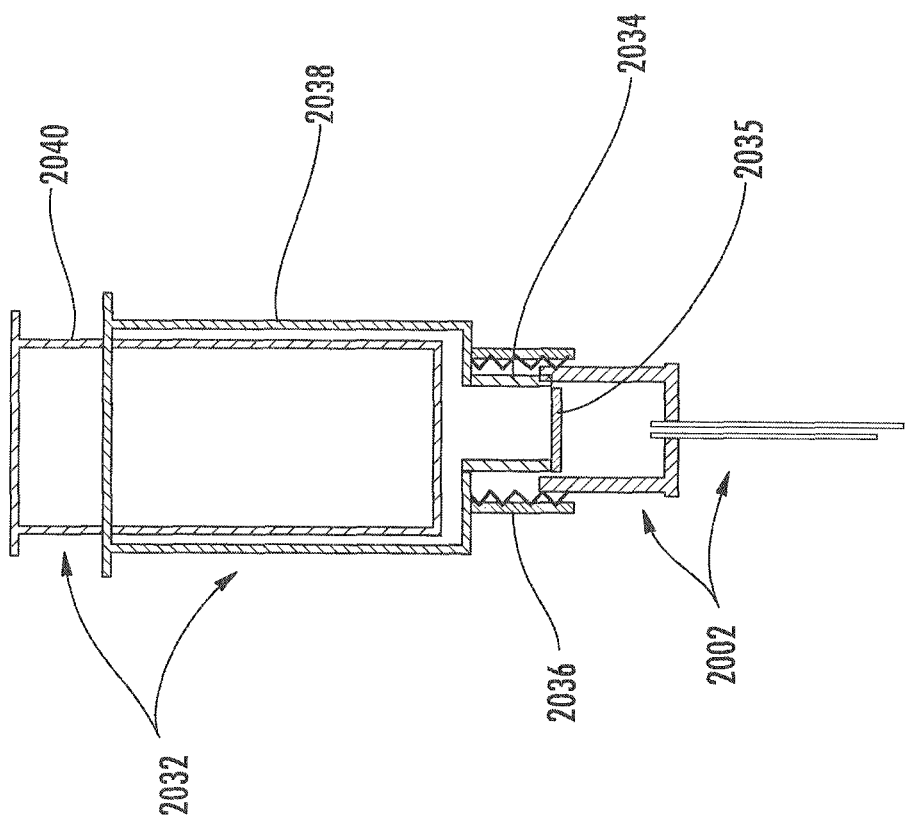

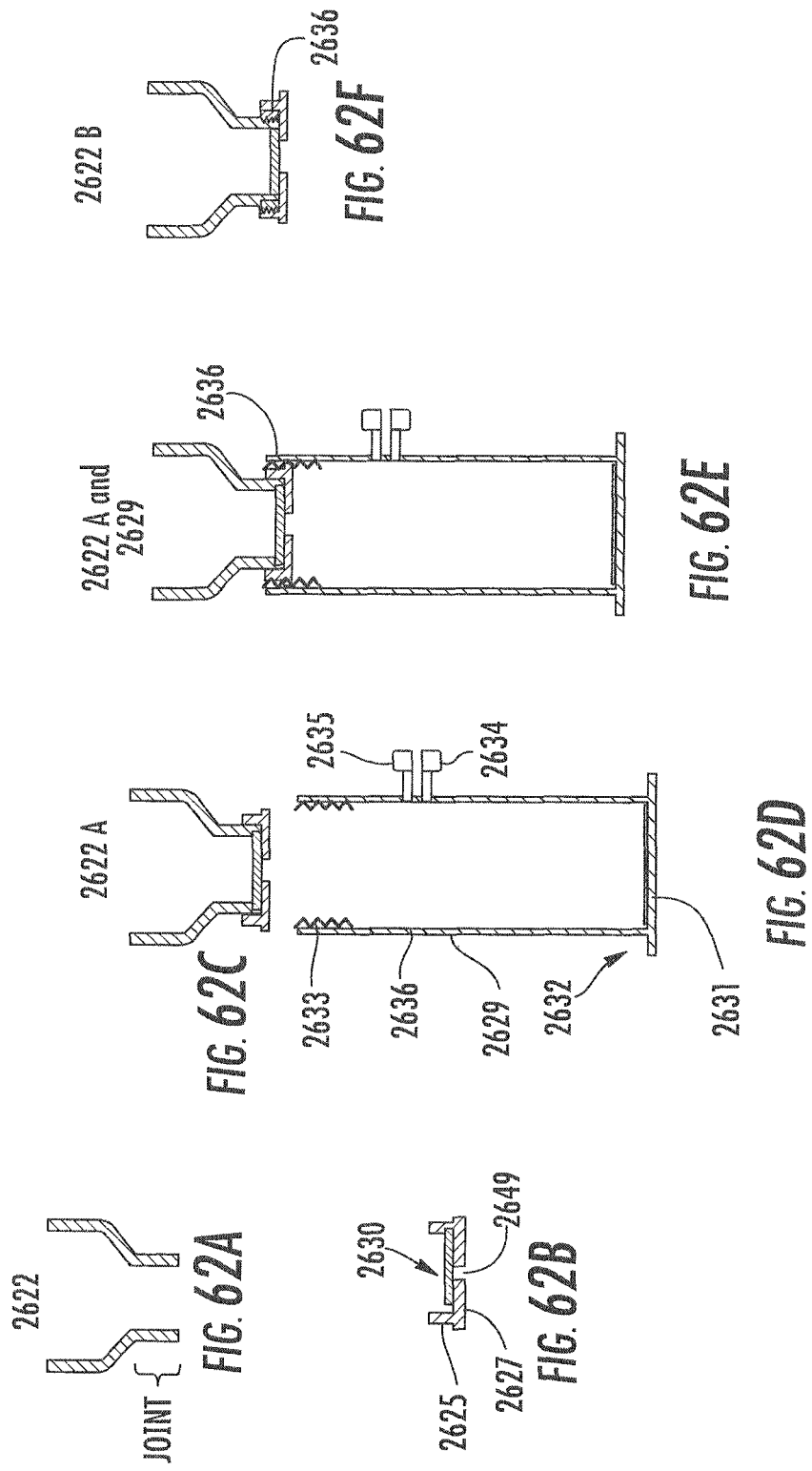

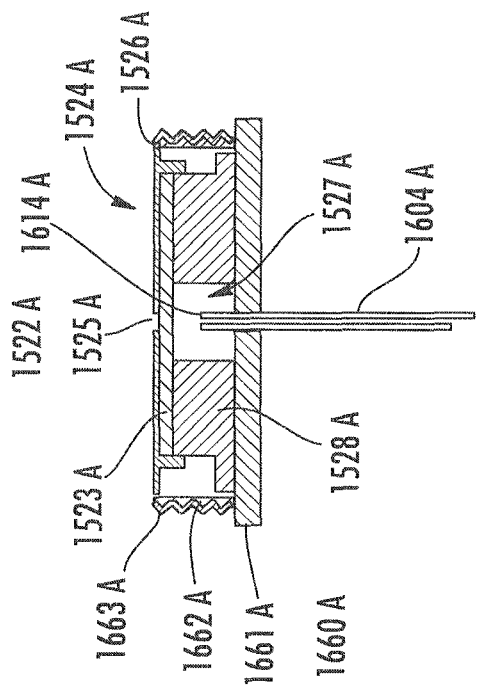
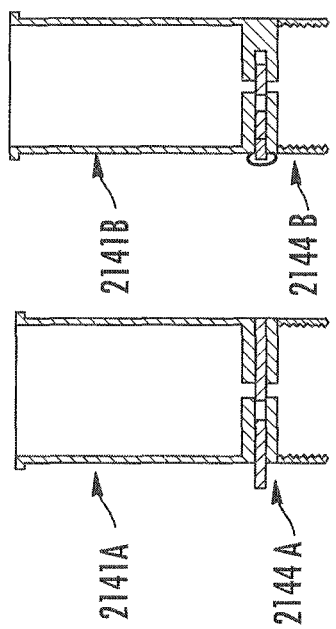
FIG. 64
FIG. 63B
FIG. 63A

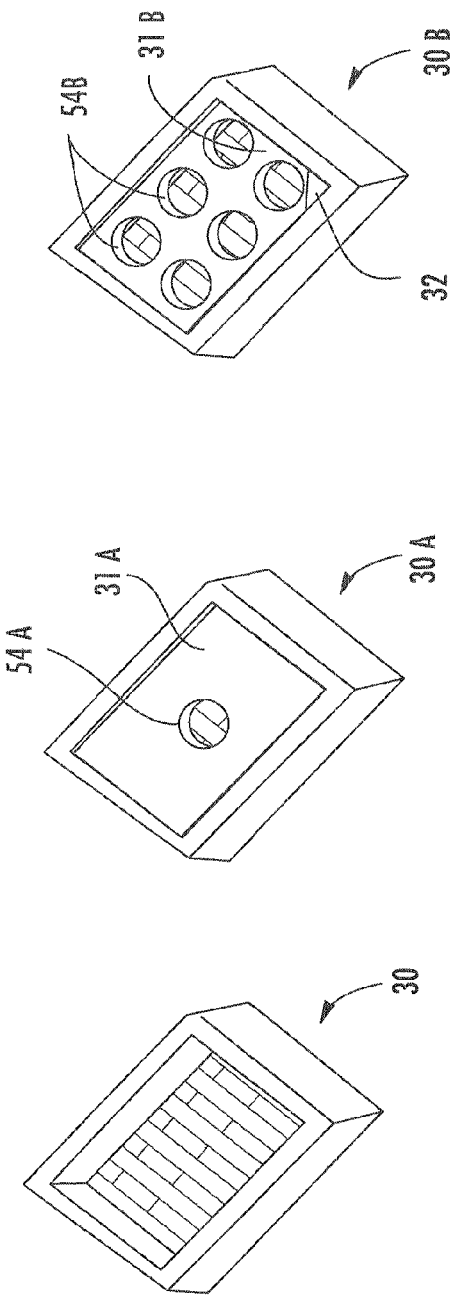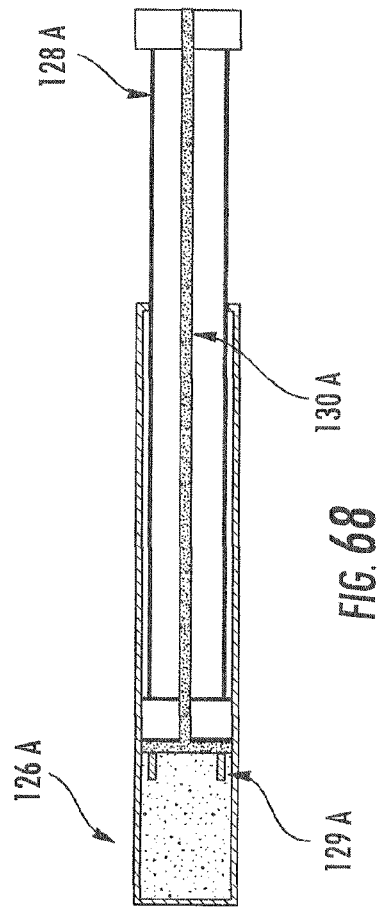

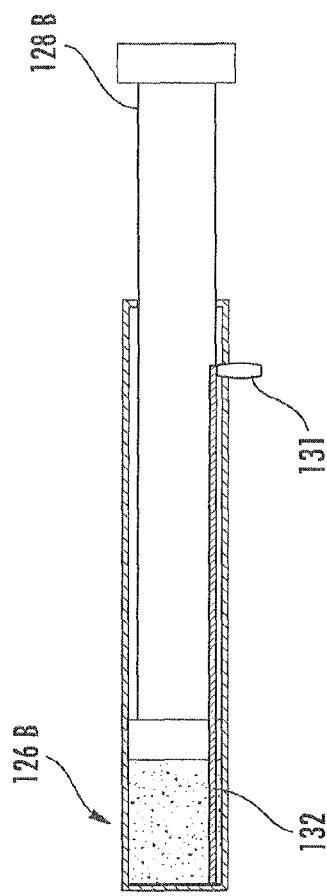
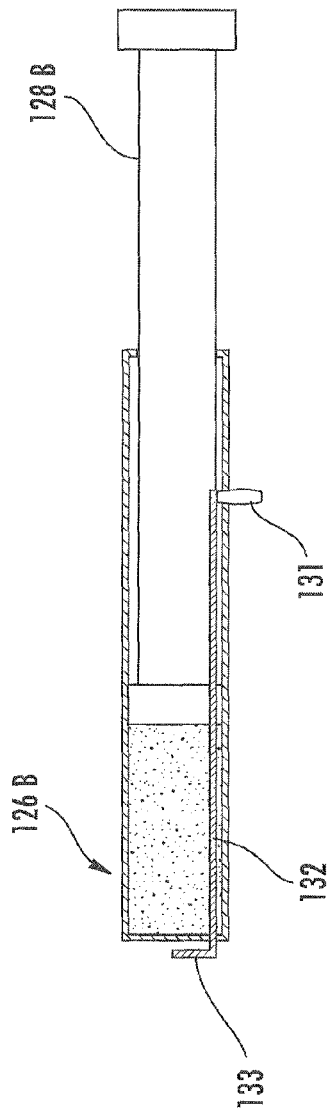

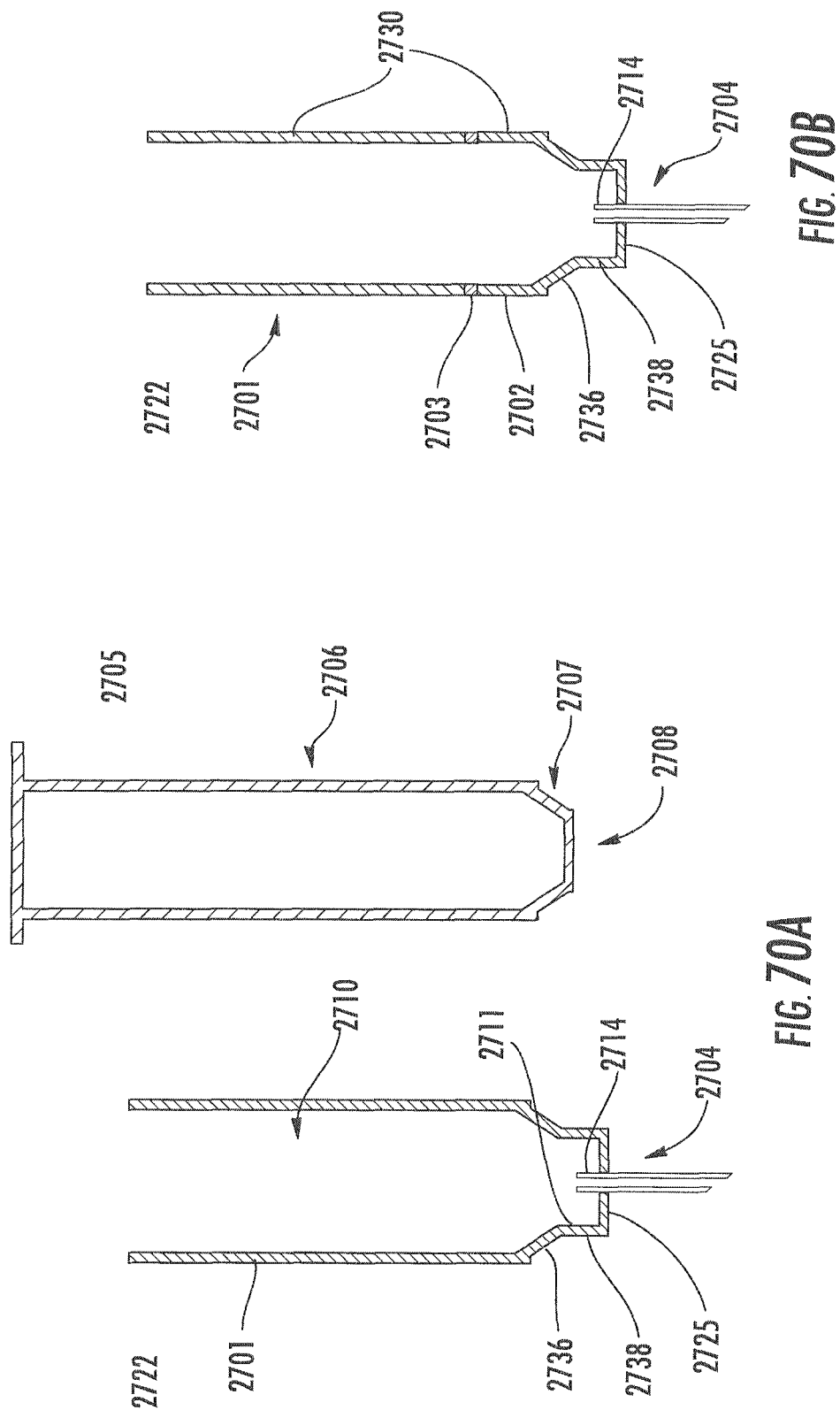

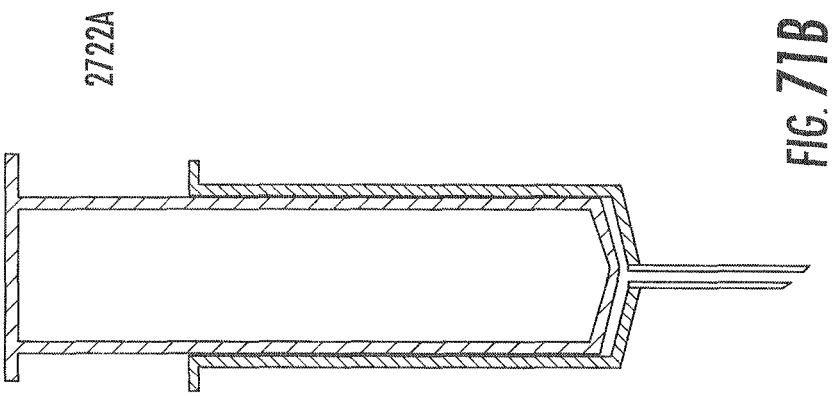
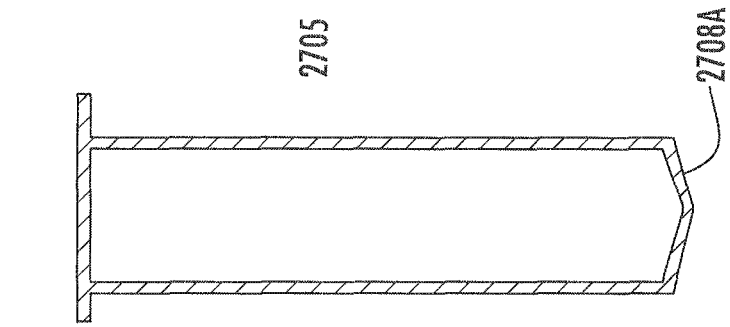
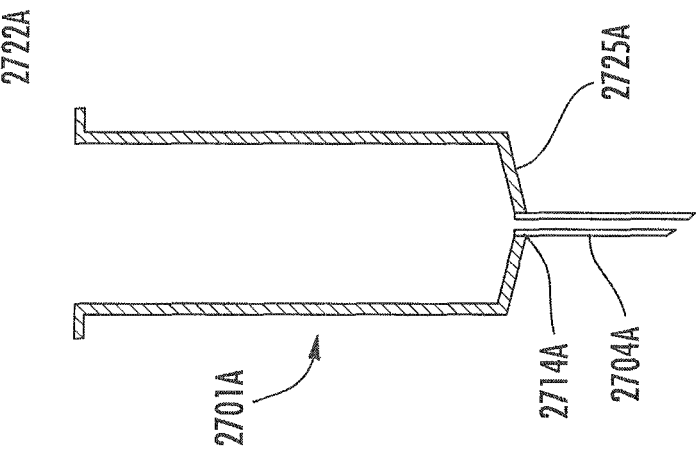

CYTOBLOCK PREPARATION SYSTEM AND METHODS OF USE

CROSS-REFERENCE TO RELATED PATENT APPLICATIONS

This is a continuation of U.S. application Ser. No. 11/688,276, filed Mar. 20, 2007, which claims priority under 35 USC Section 119(e) from U.S. Provisional Patent Application Ser. No. 60/852,798 filed on Oct. 19, 2006; U.S. Provisional Patent Application Ser. No. 60/846,036 filed on Sep. 20, 2006; U.S. patent application Ser. No. 60/801,759, filed on May 20, 2006; and U.S. Provisional Patent Application Ser. No. 60/783,881 filed on Mar. 20, 2006. This application is related to U.S. patent application Ser. No. 11/284,501 filed Nov. 22, 2005, and U.S. Provisional Patent Application Ser. No. 60/630,870, filed on Nov. 24, 2004. The contents of each of the above applications are incorporated herein by reference in their entireties.

BACKGROUND

Fine needle aspiration (FNA) is a widely used screening diagnostic procedure. Cells and tissues collected through FNA are used to make smears for quick staining and microscopic examination at the bed side and in most cases the collected cells and tissues are used to make a cell block for further studies. The current process of FNA is divided into two steps and using two separated systems respectively: The first step is sample collection and the second step is cell block preparation.

A syringe, combined with a fine needle, is conventionally most widely used as an aspiration tool in current clinical practice for sample collection.

A fine needle is briefly divided into three parts, the hub, the shaft, and the bevel. The hub is at one end of the needle and is the part that attaches to the syringe. The shaft is the long slender stem of the needle that is beveled at one end to form a point. The hollow bore of the needle shaft is known as the lumen. Disposable needles should always be used when preparing admixtures as they are presterilized and individually wrapped to maintain sterility. Needle size is designated by length and gauge. The length of a needle is measured in inches from the juncture of the hub and the shaft to the tip of the point. Needle lengths range from ⅜ inch to 3½ inches; some special use needles are even longer. The gauge of a needle, used to designate the size of the lumen, ranges from 27 (the finest) to 13 (the largest).

The fine needles used in conventionally FNA procedures have a small hub with a small space since the main function of the hub is to connect the shaft of needle to the syringe that provide a space for the storage of collected cells and tissues. The diameter of the conventional hub is less than 4 mm. During routine FNA procedure using a conventional needle and syringe, frequently, portion of the collected cells and small fragments of tissues stay in the small space of hub between the shaft of the needle and the nipple of the syringe. For majority of the FNA procedures, the stayed portion of the collected cells and tissues appears to be critical for the further studies and efficiently utilization of this portion of specimen remains as a problem. The current attempt to address this problem is to wash the syringe and the needle with a fixative (Formalin or ethanol) to remove all stayed specimen into the fixative in a container, and then separated the specimen material from the liquid fixative using centrifugation technique. After the centrifugation, supernatant (the fixative) is moved out; a matrix ("HistoGel", argrose gel or others) is added and mixed with the cell or tissue pellet to make a gel-sample mixture. The tubular container contains the mixture is put in low temperature (40 C.) for miniatures to make the mixture relatively solidified and then is moved out from the container, wrapped by a tissue paper and put into a tissue cassette for further treatment. Since only a small and finite amount of material can be obtained by FNA and the current process does not maximally use this limited amount of material. The limited amount of material collected through this procedure largely inhibits further classification of the disease, which results in more invasive procedures for a more conclusive diagnosis. This not only results in increased costs, but significantly delays the diagnosis as well.

The need remains for systems and methods which maximize the use of this limited material for different (H&E staining, immunocytochemistry and other) studies to permit a more conclusive diagnosis to be made by a single FNA procedure alone and without the need for more invasive procedures.

BRIEF DESCRIPTION OF THE DRAWINGS

FIG. 3 is a schematic of a centrifuge tube containing a fixative solution to which cellular material has been added.

FIG. 4 is a schematic block diagram illustrating the centrifugation of the centrifuge tube shown in FIG. 3.

FIG. 5 is a schematic block diagram illustrating removal of supernatant from the centrifuged specimen by use of a moisture removal device.

FIG. 6 is a schematic illustrating transfer of the cellular pellet from the centrifuge tube to a transfer tube after removal of the supernatant.

FIG. 7 is a schematic block diagram illustrating the transfer of the cellular pellet from the transfer tube into a matrix container containing a pre-warmed matrix material using a tamping device.

FIG. 12 is a schematic illustrating the placement of the gelled specimen within a well within an embedding block.

FIGS. 13A-13C are perspective views illustrating various configurations of embedding blocks and wells.

FIG. 14 is a schematic illustrating the placement of an embedding tray over the embedding block containing the gelled specimen.

FIG. 15 is a schematic illustrating the placement of the embedding tray on a warming plate.

FIG. 16 is a schematic illustrating the placement of the embedding tray on a cooling plate FIG. 17 is a schematic of an alternative embodiment of a matrix container in which the matrix container takes the form of a syringe.

FIGS. 20-27 schematically illustrates other embodiments of the kit of FIG. 2 according to example embodiments.

FIG. 28 schematically illustrates a collection system according to an example embodiment.

FIGS. 29-32 schematically other embodiments of the collection system of FIG. 28 according to an example embodiment.

FIGS. 55-65 schematically illustrates additional embodiments of the tube with associated components according to an example embodiment.

FIGS. 67 schematically illustrate different embodiments of a sponge plate according to an example embodiment.

FIGS. 68-71 schematically illustrate other embodiments of the tube of FIG. 19A according to an example embodiment.

DETAILED DESCRIPTION OF THE EXAMPLE EMBODIMENTS

Figure 1:
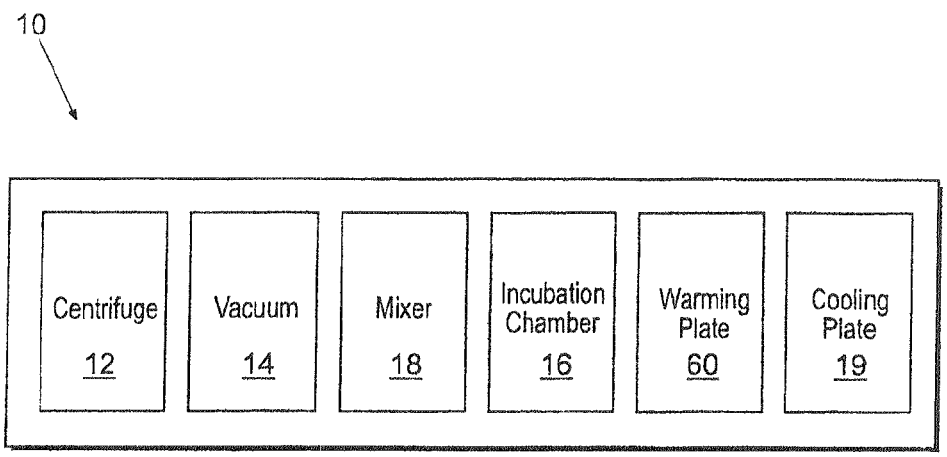
FIG. 1 is a schematic block diagram of an instrument for the preparation of a cytoblock.

FIG. 1 shows a device or instrument 10 for the preparation of a cytoblock. The instrument 10 provides the mechanical equipment necessary to process a fine needle aspiration (FNA) specimen for microscopic examination in a single piece of laboratory equipment. In the illustrated embodiment, the instrument 10 provides a centrifuge 12, supernatant and moisture removal device 14, temperature incubation chamber 16, mixing device 18, a warming plate 60, and a cooling plate 19. In the preferred embodiment the instrument 10 is integrally connected and unitary in its overall nature. However, it is also contemplated that any combination of two or more of the abovementioned components could be formed together as a unitary structure as is convenient in the laboratory setting.

Figure 2:
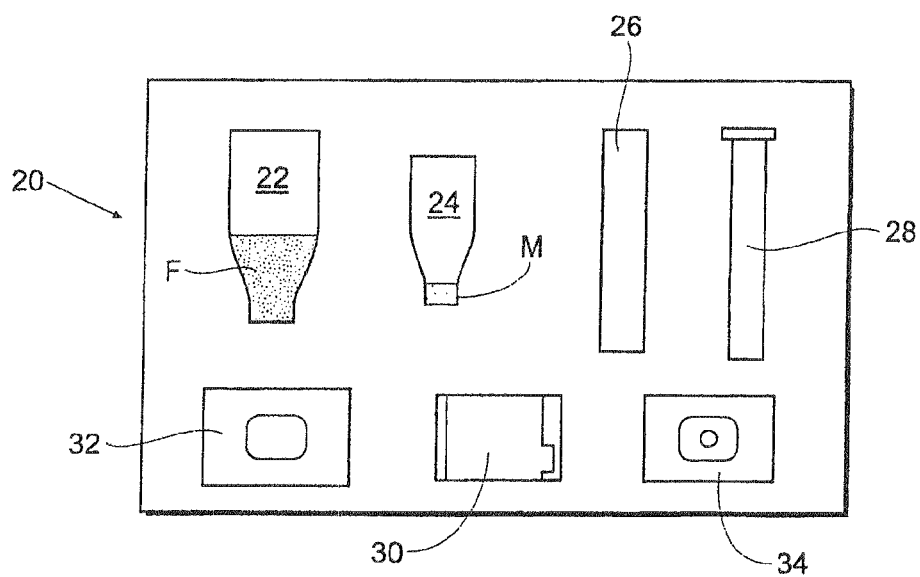
FIG. 2 is a schematic of a kit of components for use with the instrument shown in FIG. 1.

The instrument 10 is designed for use with additional materials, including disposable and/or consumable components, required for processing of the specimen, which are desirably supplied in the form of a kit 20, as FIG. 2 shows. In the illustrated embodiment, the kit 20 provides a centrifuge tube 22 containing a fixative F, a matrix container 24 containing a matrix material M, a transfer tube 26, a tamping device 28, a tissue cassette 30, an embedding tray 32, and a paraffin or other embedding block 34. It is contemplated that a kit 20 may be provided that includes any or all of these items and that the items may be provided in any desired quantity. Although in the illustrated kit 20, the transfer tube 26 and the tamping device 28 are shown separately, it is also contemplated that these two items could be provided together with the tamping device 28 inserted in the transfer tube 26, ready for use in preparing a cytoblock sample.

The instrument 10 and associated kit 20 are particularly well-suited for use in preparing and processing specimens for immunocytochemistry (ICC) studies on the limited materials collected by FNA, biopsy, endoscopic procedures, washings, and lavages and therefore will be described in accordance with such use. It will be readily apparent, however, that the instrument 10 and kit 20 are also suitable for use in other studies, e.g., special stains, in situ hybridization, RNA and DNA studies, as well as in basic research requiring the collection and saving of treated cells.

Together, the instrument 10 and kit 20 provide a system that permits the preparation of multiple sections from a single FNA. Each section contains sufficient cells or material for staining or other studies.

In use, as shown in FIG. 3, the cellular material C obtained from the FNA or other specimen is added to the centrifuge tube 22 containing the fixative F, e.g., formalin. Desirably, the tube 22 has a tapered region 36 and a non-tapered, reduced diameter bottom region or chamber 38. This configuration allows for maximal concentration of cells or specimen at the bottom of the tube 22 after centrifugation. As will be explained later, together with transfer tube 26 and tamp 28, this configuration permits easy removal and transfer of essentially all of the cellular material.

It should be noted that it is also contemplated that the cellular material C could be added to a centrifuge tube 22 which does not already contain a predetermined quantity of fixative. In such an embodiment, an appropriate quantity of fixative would be added to the centrifuge tube 22 along with the cellular material C.

The tube 22 is then placed into the centrifuge 12 for separation. In a representative embodiment, the centrifuge 12 is a conventional low speed centrifuge 12 that permits the separation of the aspirate/fixative mixture into a supernatant S and a cell pellet P, as seen in FIG. 4.

The supernatant S is then removed, as shown in FIG. 5, using supernatant and moisture removal device 14, e.g., with aspiration tubing 40 or other aspiration means, such that tube 22 retains the pellet P. It is important to remove as much of the supernatant S as possible without disturbing the pellet P. In the preferred embodiment the supernatant and moisture removal device 14 comprises a vacuum device, however alternate methods of removing the supernatant S are contemplated, including, but not limited to, using laser or heat provided by the instrument 10. The instrument 10 can also include a detector to sense the amount of moisture in the tube 22.

The matrix container 24 (which contains a viscous matrix mixture M is desirably pre-heated by placing the container 24 in the temperature incubation chamber 16. A variety of matrixes are available in the art, which include agar, agarose gel or "histogel" solid at ambient temperature, Methocell®, Matrix Gel®, OCT compounds, paraffin, denatured and non-denatured collagen, fibronectin, laminin, and mixtures thereof. Those skilled in the art will know of other suitable matrixes for cell immobilization, or will be able to ascertain such, without undue experimentation. The incubation chamber 16 may be a single chamber selectively adjustable over a broad range of temperature, e.g., between −50-100° C. Alternatively, the chamber 16 may include distinct heating and cooling chambers (e.g., a separate heating block and cold plate) that are independently adjustable within a defined temperature range, e.g., 50-100° C. and 2-8° C. respectively.

The matrix material M is pre-heated by selecting a temperature that permits liquefaction of the matrix. The incubation chamber 16 includes a well (not shown) or otherwise receives the matrix container 24 to heat the matrix material M to the desired temperature prior to adding the matrix material M to the cell pellet P. It will be readily apparent that the chamber may include a series of wells, which may be of the same or of different size and/or configuration, to accommodate multiple specimens and/or containers 24 of varying size or shape. In one embodiment, the temperature of the chamber 16 is first set to between 90-100° C. to liquefy the matrix material M. Once the matrix material M has been liquefied, the temperature is adjusted and lowered to 50° C. to maintain the matrix material M in the liquid state.

The pellet P is then removed from the centrifuge tube 22 by use of transfer tube 26 and tamp 28. The transfer tube 26 is a tube having a hollow core 42 and open end 44. The transfer tube 26 is placed into the centrifuge tube 22 and passed over the pellet P to retain the pellet within the hollow core 42, as shown in FIG. 6. The transfer tube 26 preferably has a complementary size and shape to the chamber 38 and thereby permits the collection and transfer of essentially the entire pellet P. The tamping instrument 28 desirably has end portion 46 and is sized and configured for passage through the transfer tube 26 to release the pellet P into the matrix container 24, as shown in FIG. 7. Although the tamp 28 could be formed as a solid piece, the preferred embodiment of the tamp 28 includes a hollow channel along the length of the tamp 28, passing through the center of the tamp 28. The hollow channel extends through the end portion 46. This hollow channel allows air to be released through the tamp 28. In this arrangement, the matrix container 24 desirably contains a pre-measured amount of matrix material to provide a desired ratio of matrix material M to the cellular pellet P, e.g., a 1:1 ratio.

Figure 19A:
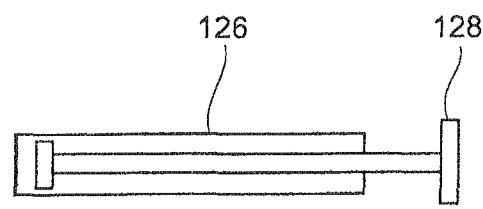
FIGS. 19A-19C are schematic views of additional embodiments of the transfer tube of the present invention.
Figure 19B:
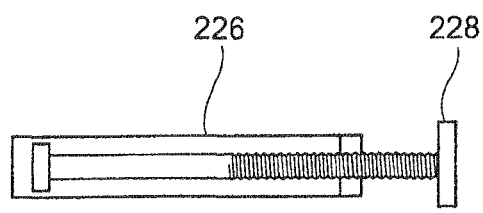
Figure 19C:
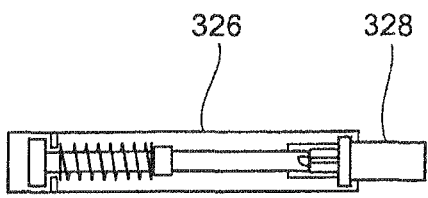

The tube 26 and tamp 28 may be reusable, e.g., formed of metal, or may be suitable for disposal after a single use, e.g., formed of plastic. Additional embodiments of the transfer tube 26 and tamp 28 are shown in FIGS. 19a-19c. FIG. 19a shows a transfer tube 126 and tamp 128 which is similar to the preferred embodiment, however, the tamp 128 has a narrow central portion. The tamp and transfer tube operate in the same manner as the preferred embodiment, wherein the tamp is pushed to advance the tamp inside the transfer tube and the tamp is pulled to retract the tamp from the tube.

Tube 226 of FIG. 19b is similar to tube 126 of FIG. 19a, however the transfer tube 226 and tamp 228 include a mating screw mechanism such that the tamp 228 is advanced in the transfer tube 226 by rotating the tamp 228 in one direction and retracted from the transfer tube 226 by rotating the tamp 228 in the opposite direction.

Tube 326 of FIG. 19c is similar to tube 26, however a spring mechanism is engaged between the transfer tube 326 and the tamp 328. In this embodiment, the tamp 328 is advanced by pushing on the tamp 328 to engage the spring. The tamp 328 is retracted from the tube 326 by again pushing on the tamp 328 to disengage the spring. This mechanism is similar to that utilized in a spring-retractable ball point pen. While the preferred embodiment discloses utilizing the transfer tube 26, 126, 226, 326 and tamp 28, 128, 228, 328 to transfer the cell specimen, it is also contemplated that the tube 26, 126, 226, 326 and tamp 28, 128, 228, 328 could have additional uses in the medical field, such as for taking dermatological biopsies.

The pellet P is then thoroughly re-suspended and mixed within the matrix material M using the mixing device 18. In the illustrated embodiment, the mixing device 18 provides a mixing probe 48, which can be positioned within and near the bottom of the tube 24 and activated to provide mechanical stirring or mixing motion. It will be readily apparent that a variety of other mixing means may be provided, e.g., a vortex.

Figure 9:
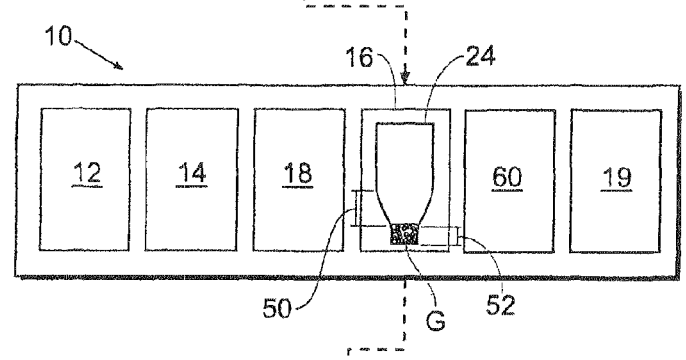
FIG. 9 is a schematic block diagram illustrating the cooling incubation of the matrix material/cell pellet mixture to form a gelled specimen.

With reference now to FIG. 9, the tube 24 is then placed in the incubation chamber 16 for a time period sufficient to solidify the specimen into a gel G. The chamber 16 receives the tube 24 to cool the matrix material M/cell pellet P mixture to the desired temperature. The temperature is desirably selectively adjustable within a range that permits solidification or gelling of the histogel, preferably from −2 to −8° C., and more preferably about −4° C.

The matrix tube 24 desirably provides a tapered region 50 and reduced diameter chamber 52 similar to centrifuge tube 22. Chamber 52 serves to form and maintain the gelled specimen G in a desired shape or configuration. In a preferred embodiment, the chamber 52 is of a round or cylindrical configuration and results in the formation of an essentially round or circular gelled specimen G. It is to be understood that the chamber 52 may be variously configured to provide a gelled specimen G of a desired size and shape, e.g., square or oval.

Figure 10:
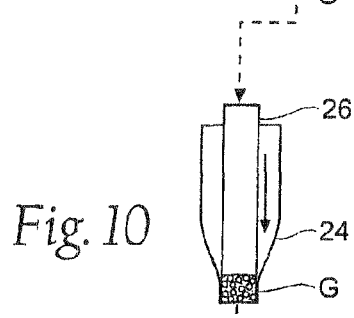
FIG. 10 is a schematic illustrating the transfer of the gelled specimen from the matrix container to the transfer tube.

After solidification, as shown in FIG. 10, the gelled specimen G is removed from the tube 24 using the transfer tube 26 and tamp 28 or other removal means. The transfer tube 26 is placed into the tube 24 and passed through the specimen G. The tube 26 retains the specimen G within the hollow core 42, much like a straw that has been passed through solid gelatin. The transfer tube 26 preferably has a complementary size and shape to the chamber 52 and thereby permits the collection and transfer of essentially the entire gelled specimen G and serves to retain the specimen G in the desired configuration. The tamping instrument 28 can then be passed through the core 42 to release the gelled specimen G, which can then be further processed, e.g., by frozen section or by embedding in a paraffin or other embedding block. It should be noted that while paraffin is the preferred embedding material, and is used throughout the description of this process, one of skill in the art will recognize that any suitable embedding material may be utilized. Embedding materials include, but are not limited to nitrocellulose, glue, denatured or non denatured collagen, fibronectin, laminin, gum syrup, OTC compounds, and various formulations of plastic polymers.

Figure 11A:
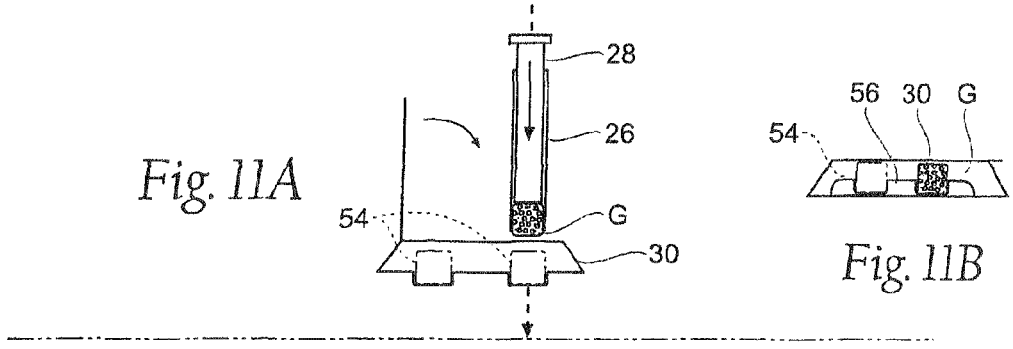
FIG. 11A is a schematic illustrating the transfer of the gelled specimen from the transfer tube to a chamber within a tissue cassette using the tamping device.

In processing the specimen G by embedding, the specimen G is then placed into the tissue cassette 30. The cassette 30 may be formed of plastic or other any other suitable material, and may be adapted for multiple or single use. As shown in FIG. 11A, the cassette 30 desirably includes a recessed well or chamber 54 to receive the specimen G. Additional chambers 54 may be provided for additional specimens or quality control samples as desired. In an alternative embodiment, illustrated in FIG. 11B, a removable basket 56 providing one or more chambers 54 is provided. The chamber 54 extend through the removable basket 56, forming aperture in the basket 56. A lid or other cover (not shown) may be provided to cover the chamber 54 and further secure the specimen G within the cassette 30. The chamber 54 is preferably similar and complementary in size and configuration to the chamber 38 and specimen G so as to retain the specimen G in the desired configuration during subsequent processing.

The removable basket 56 preferably has at least one cylindrical chamber 54 integrally formed therein. However, it will also be readily apparent that the size, number, and configuration of the chambers 54 of the basket 56 may be varied to accommodate the procedures being performed and the number and types of specimens being processed. The removable basket 56 could be made of any suitable material, including, but not limited to plastic or foam.

After processing, the specimen G is transferred from the cassette 30 into a pre-bored hole or well 58 within the embedding block 34, as FIG. 12 shows. Block 34 is desirably provided with at least one pre-bored hole to receive the prepared gelled specimen G. FIGS. 13A-13C provide, by way of example and not limitation, possible configurations of embedding blocks 34 and wells 58. It will be readily apparent that the block 34 may be of any suitable size and configuration, e.g., rectangular (FIGS. 13A and 13B) or square (FIG. 13C). It will also be readily apparent that the size, number, and configuration of wells 58 may be varied to accommodate the procedures being performed and the number and types of specimens being processed, e.g., a single block 34 may provide wells 58 of different sizes (FIG. 13A).

In an alternative embodiment, block 34 may be provided in kit 20 without pre-bored wells 58. In this arrangement, transfer tube 26 is preferably formed of metal or otherwise adapted to bore through the block 34 to form a well 58 or series of wells 58 so that the number and placement of wells 58 may be determined by user.

The embedding tray 32, which is desirably complementary in size and shape to block 34, is placed over the block (FIG. 14). In the illustrated embodiment, the tray 32 is a conventional embedding tray and may be formed of metal, plastic or other suitable material and may be suitable for single or multiple use.

The tray 32, containing block 34 with specimen G, is then inverted and placed on the warming plate 60 (FIG. 15) or otherwise warmed to provide sufficient liquefaction to fill and essentially eliminate well 58 and thereby embed the specimen G. The temperature of the warming plate 60 is desirably selectively adjustable within a range that permits sufficient liquefaction, e.g., from 55 to 65° C.

In an alternative embodiment, wells 58 may be closed and the specimen G firmly embedded by pipetting or otherwise delivering heated, liquefied paraffin without use of the tray 32 (not shown). The paraffin may be pre-heated and liquefied by placing on warming plate 60, microwaving, or other suitable means.

Figure 18:
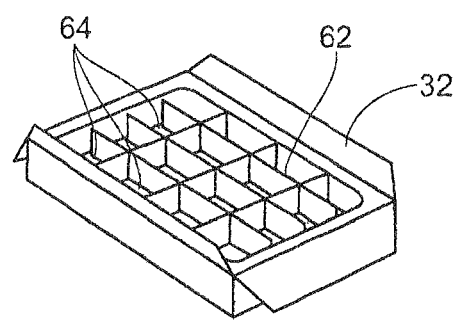
FIG. 18 is a schematic view of an embedding tray including a dividing insert.

In an additional alternative embodiment, the tray 32 may be provided with a partitioned insert 62 which includes multiple divisions 64, as shown in FIG. 18. In use, the insert 62 is first placed in the embedding tray 32. At least one specimen G may then be placed in each partition 64 of the insert 62. The specimen G is embedded by pipetting or otherwise delivering heated liquefied paraffin to the tray 32. The tray 32 is then cooled to form a solidified block 34. Alternatively, the tray 32 can be filled with paraffin before the insert 62 is placed in the tray 32. After the insert 62 is placed in the paraffin on the tray 32, at least one specimen G can be placed in each partition 64 of the insert. The tray 32 is then cooled to form a solidified block 34.

The tray insert 62 may have any suitable number and configuration of divisions 64. The tray insert 62 may be made of any suitable material, including, but not limited to plastic or metal. This configuration would be particularly useful in creating a cell array containing cell samples from multiple origins, as is further described below.

The block 34 can then be placed on the cooling plate 19 or otherwise cooled to solidify the block 34 (FIG. 16). The temperature of the cooling plate 19 is desirably selectively adjustable within a range that permits solidification, e.g., from −50 to +4° C. The block 34 may then be and removed from tray 32 for further cytological or histological processing, e.g., cutting of the prepared block 34 and preparation of slides for staining or other diagnostic techniques. The cooperating and complementary components of the described system, in particular the chambers 38 and 52, transfer tube 26 and tamp 28, and well 58 serve to retain the embedded specimen G in the desired shape, e.g., cylindrical. Because the desired shape has been maintained throughout processing of the specimen, a consistent and uniform number of cells or material is provided on each slide. As a result, more diagnostic procedures may be performed from a single FNA or other specimen, reducing the need to obtain additional specimens and thereby also reducing the need for more invasive procedures. However, it can be appreciated that although a cylindrical shape is preferred, the configuration can be in any suitable shape, provided that the chambers 38 and 52, transfer tube 26 and tamp 28 and well 58 are all formed with the same desired shape.

FIG. 17 illustrates an alternative embodiment of a matrix container 24A in which the container 24A takes the form of a syringe. Matrix container 24A may be placed in the heating device 16 or otherwise pre-warmed to liquefy the matrix material M. The desired amount of matrix material M may then be delivered directly into the centrifuge tube 22 containing the pellet P (see also FIG. 5). In this arrangement, the container 24A may include sufficient material M for preparing more than one sample and designed for reheating and reuse. In one embodiment, the incubation chamber 16 includes a well (not shown) or other means for holding the container 24A during both warming and delivery of the material M. The pellet P is then thoroughly mixed and cooled within the centrifuge tube 22 as previously described with reference to FIGS. 8 and 9 respectively. The gelled specimen G may then be transferred to the cassette 30 using the transfer tube 26 and tamp 28, as also previously described with reference to FIG. 10. It is further contemplated that the matrix material could have a dye added, so that the paraffin is readily distinguishable from the cell mixture.

While the preferred embodiment of the invention utilizes cells obtained by fine needle aspiration, it should be clear to one of skill in the art that cellular material captured by other means could also be utilized to create a cytoblock. Cell material could also be collected by endoscopy, including but not limited to arthroscopy, bronchoscopy, colonoscopy, colposcopy, cystoscopy, ERCP (endoscopic retrograde cholangiopancreatograthy), EGD (esophogealgastroduodensoscopy), endoscopic biopsy, gastroscopy, laparoscopy, laryngoscopy, proctoscopy and thoracoscopy. Cells could also be obtained from lavage procedures, including but not limited to bronchoalveolar, breast ductal, nasal, pleural, peritoneal, gastrointestinal, arthroscopic, and urinary bladder lavages. It is also contemplated that cells could be collected from catheters such as those used in infusion, cardiovascular, rental, bladder, urethral, hemodynamic monitoring, neurological, and other procedures which would be obvious to one of skill in the art.

It is difficult to screen the expression level of a gene or molecule in different cell lines, especially for newly described ones. The current routine methods for this purpose include western blot, immunocytochemical study using fluorescence-labeled antibodies, real-time RT-PCR, northern blot, in-situ hybridization, etc.

The current sources of cells for research include commercial or privately-maintained sources of viable cells in culture, frozen viable cells of specific cell lines, and primary cultured cells derived from different organs/tissues from different organisms, plants, animals and/or human. It is very difficult and expensive to maintain these cells for scientists and researchers. A "Fixed or Permanent Cell Bank" may be provided to improve the current system and forms of cell sources. In this system, all cells from different possible sources (commercial companies, primary cultured cells derived from animals or other sources, etc.) are cultured, collected, fixed with a fixative (formalin, alcohol, et. al) and embedded in paraffin or other materials to form a long-lasting (permanent) form of cell source. Based on this principle, different cells can embedded individually like an individual account, and different cell cultures can be together to form a "Cell Bank".

It is contemplated that a variety of cell lines can be collected and embedded in paraffin blocks 34. Cultured cells may first be embedded in paraffin by conventional or by the above-described methods.

A portion of the paraffin embedded cells may then be taken out by various methods (e.g., by use of transfer tube 26 and tamp 28) and re-embedded in a paraffin block 34 as above-described to generate paraffin-embedded cell blocks 34 in a fashion of tissue microarray. It is preferred that the method of embedding including the embedding tray and partitioned tray insert is utilized to create the cell array.

Various types of arrays could be created by the above described method. By way of example, and not limitation, these types of arrays include embryonic cell array, adult cell array, primary cell array, cell line array, tissue array, mammalian array, zoo array, personal cell array, genetically altered array, chemically treated array, or disease cell array. Further it is contemplated to create a cell array by the above described method wherein the different cell mixtures differ in one or more of the characteristics selected from the group consisting of genotypic characteristics, species, origin, developmental stage, developmental origin, tissue origin, chemical treatment, cell-cycle point and disease state.

The blocks 34 may contain different combinations of different cells from different systems and organs. By way of example and not limitation, different breast cancer cell lines can be provided in one block, different carcinoma cell lines in one block, different sarcoma cell lines in one block, different benign cell lines in one block, different epithelial cell lines in one block, and different mesenchymal cell lines in one block. It is also contemplated to create a cell array with cell populations from several different types of body tissues in one cell array, the tissues including but not limited to blood, muscle, nerve, brain, heart, lung, liver, pancreas, spleen, thymus, esophagus, stomach, intestine, kidney, testes, ovary, hair, skin, bone, breast, uterus, bladder, spinal cord, and body fluids.

Cells from many cell lines, including cells from primary cultures, cells from humans, rats, mice, and other animals, cells from different organisms, and cells from an organism at different stages of development, may thereby be provided in a single cell block. The cells may be treated with different conditions (different chemicals, different temperatures, different culture conditions, etc.) based on specific requirements, collected, and embedded in a single block 34.

A variety of cell lines may be maintained as a "cell bank" and blocks 34 containing specific cell lines may be pre-formed and provided as "ready to use" blocks 34 to researchers or others. Pre-made blocks 34 including the desired embedded specimens or cell lines may be customized (e.g., specific cell line(s) and number of wells) and manufactured according to the user's specific needs.

Sections can then be generated from different blocks 34 and slides containing the cells from these sections can be obtained and processed as desired, e.g., protein, DNA, RNA, or other studies.

Figure 20:
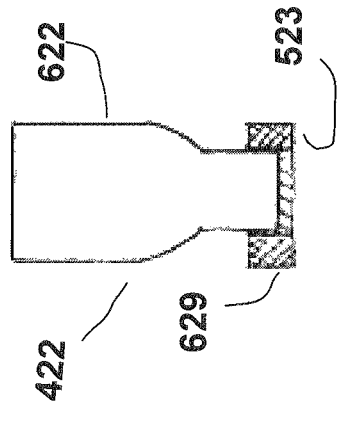

FIGS. 20-27 illustrate other embodiments of centrifuge tube 22. FIG. 20 illustrate tube 422. Tube 422 is similar to 22 except that tube 422 has an open end 423. As a result, the removal of supernatant and fluid from tube 422 is facilitated using gravity.

Figure 21:
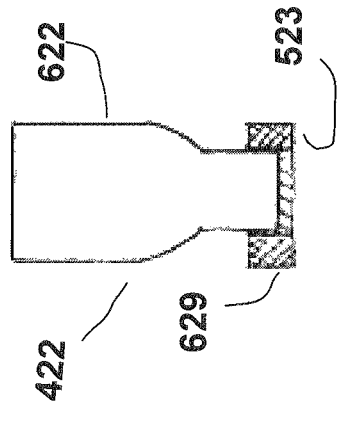

FIG. 21 illustrates filtering unit 522. Filtering unit 522 is similar to tube 422 except that filtering unit 522 additionally includes filter 523 positioned within opening 423 of tube 422. Filter 523 may comprise a piece of specific glass wool, glass fiber, paper, membrane, plastic or metal net with or without an additional supporting web. This filter will have a certain cut off spaces so that it can hold the cells, cell debris, cell organelle or cell secretion materials but will allow the water run through the filter at certain speed of centrifugation. However, the filter can be designed to hold the mix of cell and matrix at the regular condition (without centrifugation force) or supplied by a vacuum system at the bottom or using a tamp to push the fluid running through the filter. The filter can be fixed on the bottom of the tube or removable from the open-ended tube.

In other embodiments, filter 523 may be provided with a cut off spaces or filter openings having a size and density so as to allow the fluid to pass through, even without centrifugation. After the fluid running through its the filter, the filter 523 will be covered and sealed by a layer of material (gel, Vaseline, plastic tape, paper tape, et. al.) or the spaces of the filter will be filled by specific materials (gel, Vaseline, petrolatum, et. al) from the bottom of the filter and in this way the matrix and the mixture of cell and matrix will be hold inside the tube without leakage.

Figure 22:
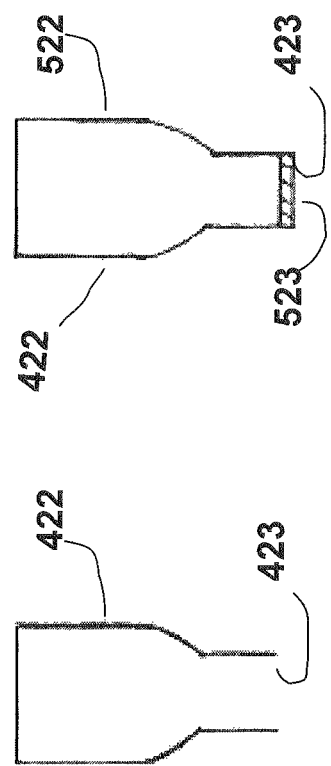
Figure 23:
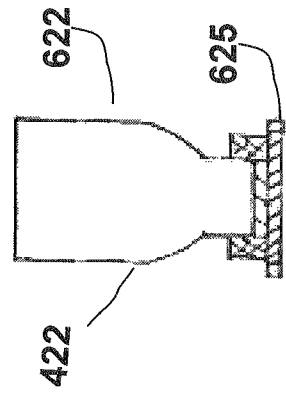
Figure 24:
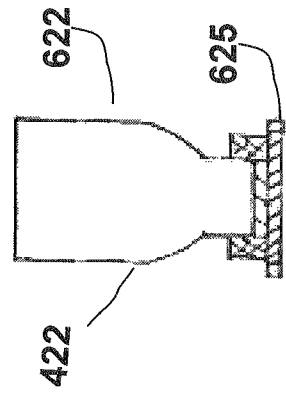

FIG. 22 illustrates filtering unit 622. Filtering unit 622 is similar to filtering unit 522 except that filtering unit 622 additionally includes a plug 629. Plug 629 is coupled to filter 523 and secures filter 523 at the bottom to the open end of the tube 422. Plug 629 is coupled to tube 422. In particular embodiments, plug 629 is coupled to tube 422 in different manners such as with a friction fit, snaps, hooks, screw threads in the like. For example, FIG. 23 illustrates filtering unit 722 in which plug 629 is coupled to tube 422 by a friction fit (pushing). FIG. 24 illustrates filtering unit 822 in which plug 629 is coupled to tube 422 via screw threads.

Figure 25:
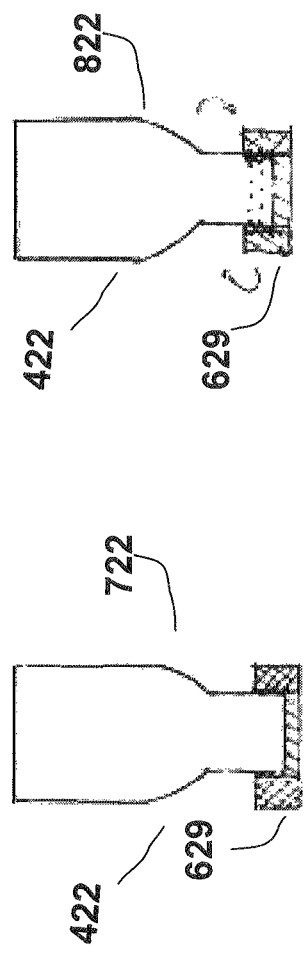

In operation, as shown by FIGS. 25 and 26, after the fluid has passed through the filter 523 (as shown in FIG. 28), a sealing material 625 may be placed across filter 523. Sealing material 625 may comprise a tape, gel material or other materials which can prevent water leakage can be used to seal the any open spaces in the filter.

Alternatively, as shown by FIG. 27, a second plug 628 which contains materials 627 such as petroleum jelly (Vaseline) or sticky tape or others can be used to cover the first plug from the outside. Then the matrix material can be added in the tube and a cell-matrix mixture will be made. After cooling down at lower temperature (4° C.), the mixture can be moved out by either punching out or by a different way, for example, move the plugs out of the tube to let the end of tube open again and pushing the mixture out from the open end by using a plunger from the top to the bottom of the tube 422. The mixture will be directly placed in the hole of the specifically designed cassette.

FIG. 28 illustrates the collection of supernatant and fluid after it has passed through filter 523. In particular, FIG. 28 illustrates tube 422 removably coupled to a collection system 927. Collection system of 927 is configured to collect fluids after they have passed through filter 523 such that the collected fluids may be reused in case there is a leakage of the filter or for other purposes. In the embodiment shown in FIG. 28, collection system 927 includes container 929. As shown by FIG. 28, container 929 has a mouth 931 configured to receive a lower end of tube 422. In the example illustrated, mouth 931 is configured to support a shoulder 933 of tube 422 during filtering. In other embodiments, the size and shape of the container 929 can be different. Container 929 can be made of different materials.

Figure 30:
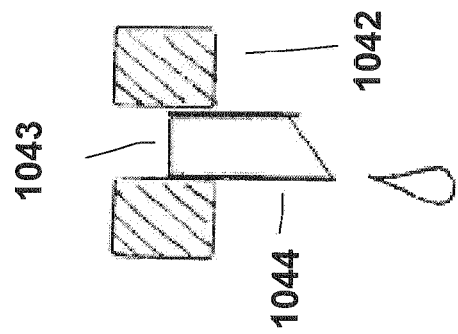
Figure 29:
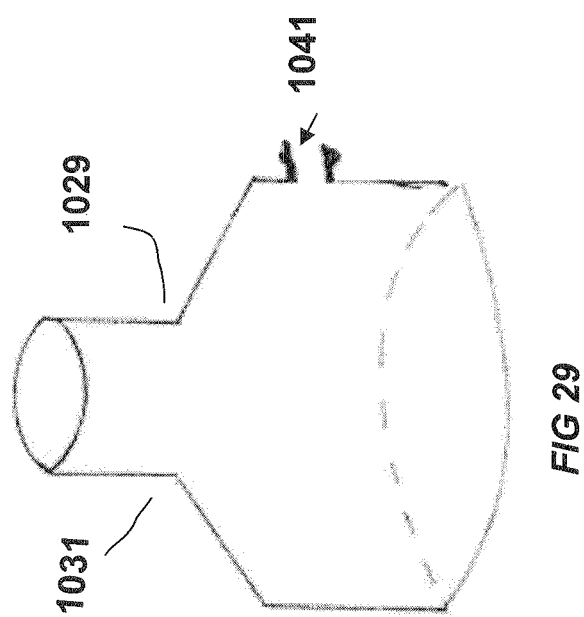

FIGS. 29-32 illustrate other embodiments of collection system 927. FIGS. 29-31 illustrate collection system 1029. As shown by FIGS. 29 and 30, collection system 1029 includes vacuum device 1031 and plug 1042, vacuum device 1031 comprises a bottle-like device with a narrower upper open end. The shape of the opening can be round or other specific shapes. The lower portion of the device is larger and the bottom end is also opened. It also could be in different shapes and sizes. But the edges of the openings should be smooth. At one side of the device, there is a hole or opening which can be used to connect to the vacuum 1041.

As shown in FIG. 30, plug 1042 is designed to cover the upper opening of the bottle-like device. The plug 1042 is divided into two portions. The lower portion has an exact size and shape to fit into the upper opening of the device 1031 without air leakage from the connection areas. The upper portion of the plug 1042 is designed with a specific size and shape to fit the tube 422. There is a central opening 1043 in the plug 1042 to allow portion of the tubes fit in and allow the fluid run through at a vacuum. There could be a tube 1044 with one end located inside the lower portion of the central hole of the plug, with another end toward to the bottom of the device. The length of the tube can be different.

FIG. 31 illustrate collection system 129 assembled. As shown by FIG. 31, collection system 1029 additionally includes support 1033 collection container 1030. In the example embodiment illustrated, support 1033 comprises a flat, soft and water-proof cushion (or mat or pad). The size of the cushion should be larger than the lower end of the bottle-like device.

Collection container 1030 collects fluid drawn through plug 1042 as a result of vacuum applied to an interior of device 1031. In practice, container 1030 is positioned at the center on the cushion, and put the lower end of the device on the cushion with the central tube toward the container. When the lower end of the bottle-like device is put on this cushion, the bottom of the device is automatically sealed and there is no air leakage from the connation between the device and the cushion. In this case, a vacuum will be generated inside the device if the vacuum is supplied through the side opening of the device. The bottle-like device 1029, plug 1042 and the cushion 1033 can be made of different materials. They could be made of glass, plastic, rubber, fibers, and other materials.

FIG. 32 illustrates collection system 1129, another embodiment of collection system 1029. Collection system 1129 is similar to collection system 1029 except that collection system 1129 includes container 1131 in lieu of container 1031. Container one 131 is similar to container 1031 except that container 1131 has a closed bottom so the fluid from each sample cannot be recollected individually. Alternatively, as shown by FIG. 32, a port or opening 1133 can be made at the lower portion of the device and a tube 1135 can be connected to the opening to allow the collected fluid run out of the device.

Figure 33:
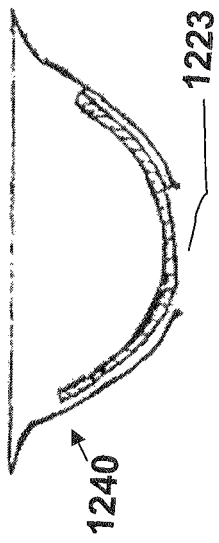
FIGS. 33-36 schematically illustrate another embodiment of the collection system of FIG. 28 according to an example embodiment.
Figure 34:
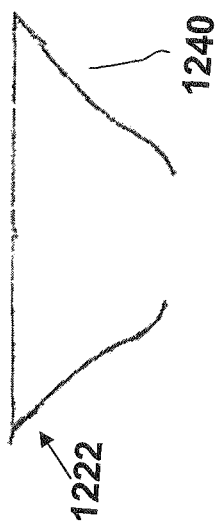
Figure 35:
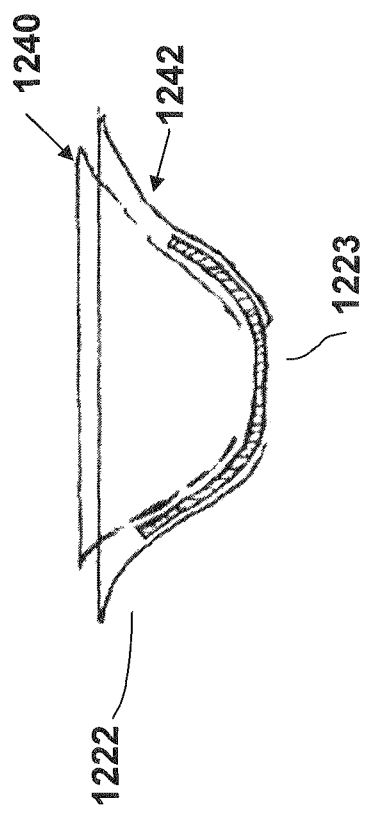

FIGS. 33-36 illustrate filtering unit 1222 and collection system 1229. Filtering unit 1222 and collection system call 29 are configured to treat larger volumes of specimens. Filtering unit 1222 comprises another embodiment of filtering unit 522. As shown by FIGS. 33-35, filtering unit 1222 comprises a double-tray device that is composed of two trays 1240, 1242 with either identical or similar shape so that one tray can be closely attached to another one. But the two trays could be in different size from each other. The central and also the bottom areas of the trays are opened. There is a filter 1223 (A piece of specific paper, membrane, plastic or metal net or other materials) is placed between the two trays and cover the opened areas of the trays. This tray-filter-tray sandwich type device can be used as a unit. The upper portion of the plug of the vacuum system can be designed to fit the outside tray so when the double-tray device is put on the plug, they fit each other very well without air leakage.

Figure 36:
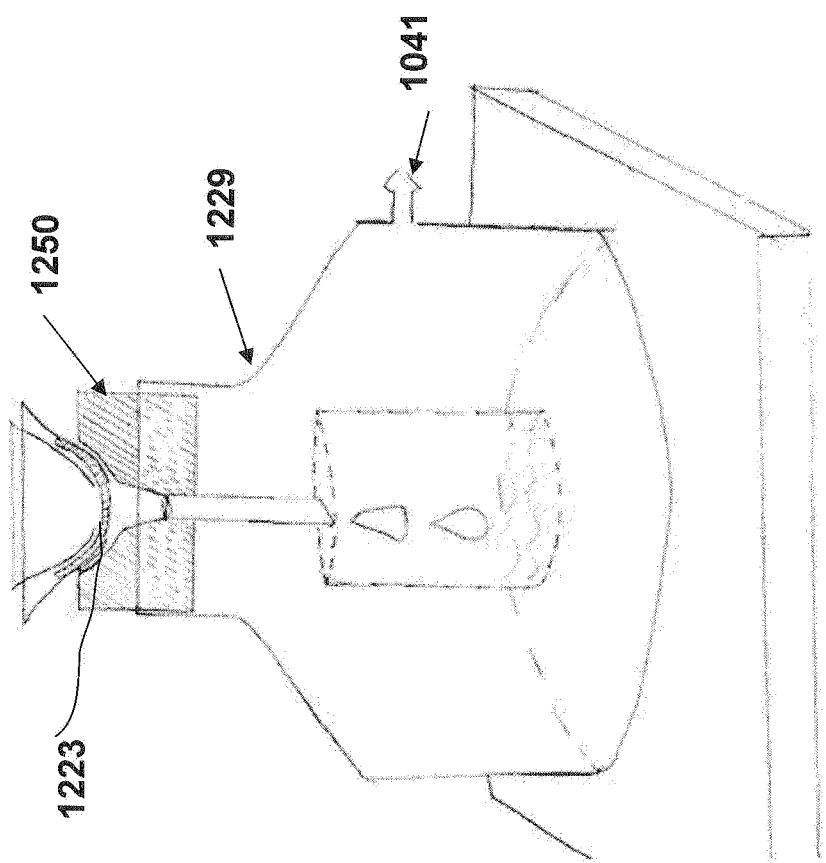
Figure 38:
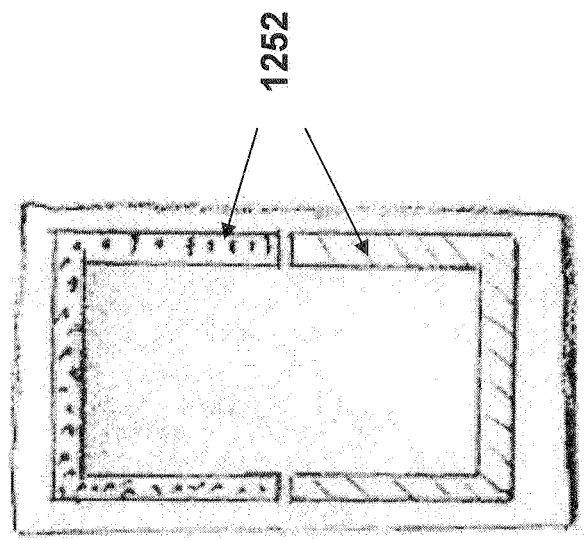
FIGS. 37-40 illustrate embodiments of a filter of the collection system of FIGS. 33-36 according to an example embodiment.
Figure 37:
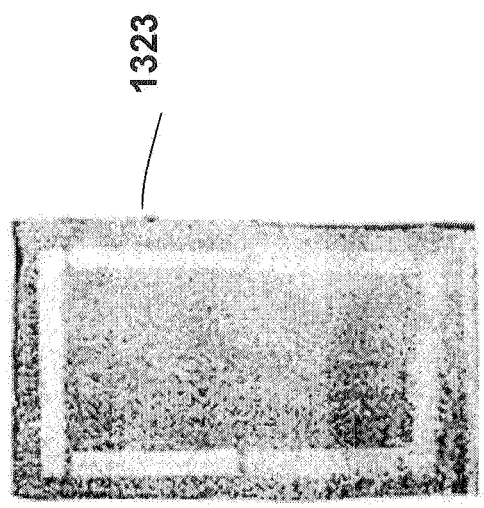
Figure 40:
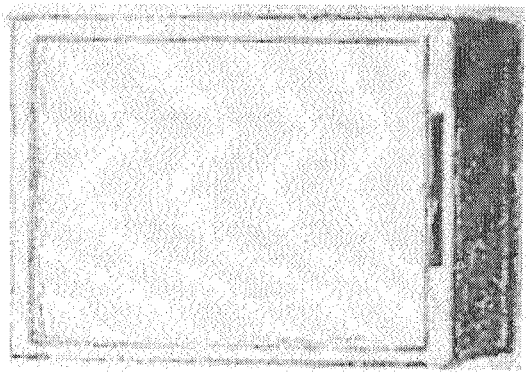
Figure 39:
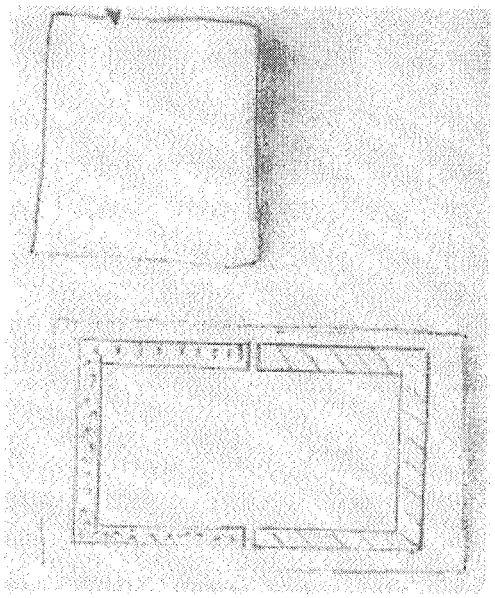

As shown by FIG. 36, collection system 1229 is similar to collection system 1029 except that collection system 1229 includes plug 1250, which is similar to plug 1042 except that plug 1250 is specifically configured to at least partially received and support filtering unit 1222. As further shown by FIG. 36, once the filtering unit 1222 is put on the plug 1250 and the vacuum system begins to work, the sample will be added to the tray and the fluid with run through the filter and the tissue or cell materials will be hold by the filter. The inner tray will be moved out, the materials remained on the filter will be wrapped up using the same filter and will be put into the cassette for next treatment. The trays can be in different size and shape and made of different materials (plastic, paper, filter paper, fibers, and others).

Alternatively, a single tray device can be made with one of the described trays covered with a filter; however, there is no second tray to cover the filter. In both devices, the filter is removable from the tray and can be wrapped.

FIGS. 37-40 illustrate other embodiments of filter 1223. In particular, FIGS. 37-40 illustrate filter 1323. Filter 1323 is pivotable are actuatable between an open position and a closed position thus to form a closed or sealed volume. The filter material (clothe, fiber, plastic, metal et. al) is attached with a strip of fastener. The filter can be folded and sealed by the fastener 1251 to form a bag-like structure which can be opened and unfolded in need. The sealed, bag-like filter can be put into the cassette directly. Alternatively, the filter can be folded and sealed by a sewing machine-like device, a stapler, a heater device or other techniques. In the example illustrated, perimeter portions of filter 1323 include opposite portions of a hook and loop fastener system (VELCRO). In other embodiments, other permanent or non-permanent attachment or fastening devices may be employed in lieu of VELCRO.

Figure 41:
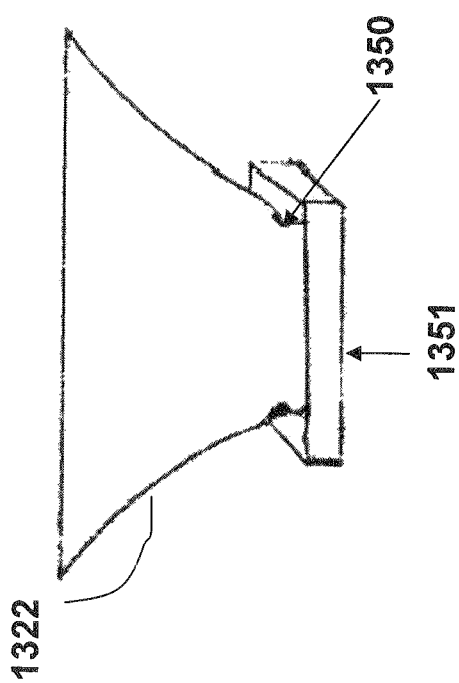
FIG. 41 schematically illustrates a tray device according to an example embodiment.

FIG. 41 illustrates an embodiment in which a single tray device 1322 can be made in a fashion of funnel: the bottom potion of the tray is opened with a protruded edge 1350 in a specific size and shape that allows the edge be put into the tissue cassettes 1351 directly without filter. In this case, the fluid which contains the small tissue fragments can be poured directly into the funnel-like single tray and the fluid will run through the bottom of the cassette and the tissue fragments will be collected directly inside the cassette.

These devices can not only used to treat cytology specimens, but also can be used to treat specimens of surgical pathology such as endocervical curettage and other surgical curettage specimens.

Alternatively, instead of using the vacuum system, the tubes and trays can be directly put on papers, paper towels, sponges or other liquid absorption materials to help the fluid run through the filters.

Figure 42:
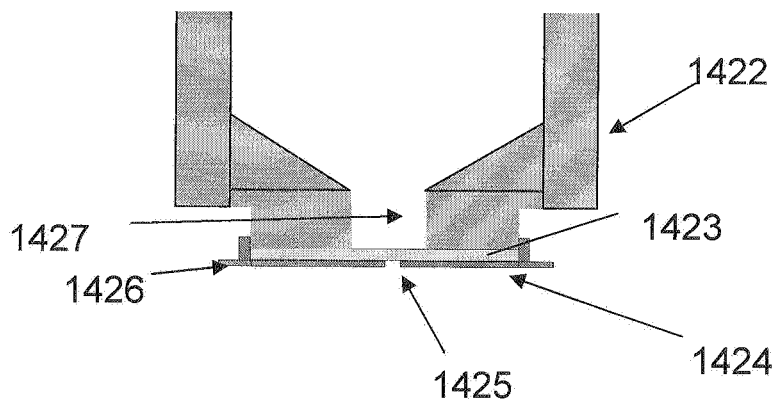
FIGS. 42-54 schematically illustrate other embodiments of the tube of the kit a FIG. 2 according to an example embodiment.

FIG. 42 illustrates modified sample tube 1422. Tube 1422 is similar to filtering unit 622 except that the plug 1424 contains a hole (or multiple small holes) 1425 and a protruding area 1426 which may function as a part of screw and as a holder and it can be used to separate the plug from the tube by pulling the plug out of the tube. The lumen of the tube has a non-tapered, reduced diameter bottom region or chamber, called sample collecting chamber 1427.

Figure 43:
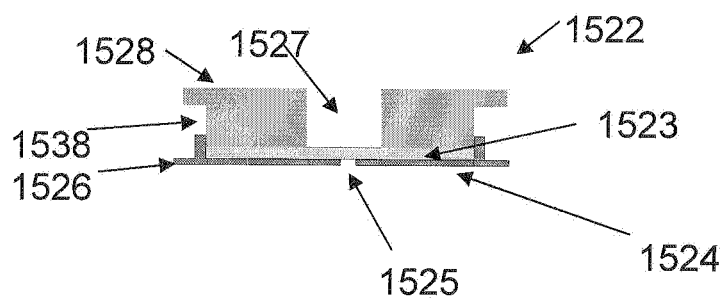

FIG. 43 illustrates modified sample tube 1522. Tube 1522 is similar to sample tube 1422, the centrifuge tube 22 and filtering unit 622 except that 1422 contains only the non-tapered, reduced diameter bottom region or chamber 1538 with a non-tapered, reduced diameter, cylindrical lumen, called as sample collecting chamber 1527. This chamber has been descript and labeled as 38 in the tube 22 in FIG. 3.

Figure 44:
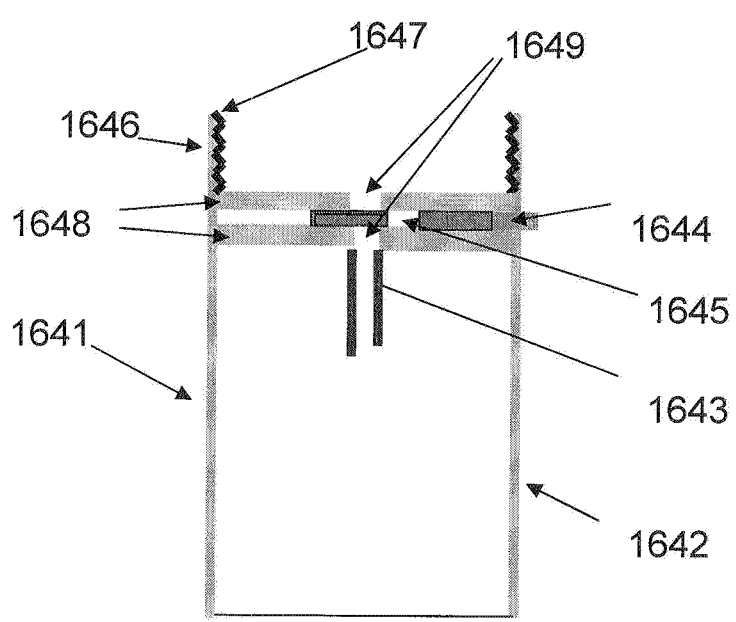

FIG. 44 illustrates a frame of device 1641 which contains a barrel 1642, a inner needle 1643, a valve 1644 with a hole

1645, a sample tube holder 1646 with a screw 1647 and a septum 1648 with a hole 1649.

Sample tube 1422 can be directly connected to a frame of the device 1641 in a manner of screw system composed of the protruding area 1426 and screw 1647 in the frame. The hole 1425 in the plug 1424 will connect to the hole 1649 in the septum 1648 of the frame 1641. The vacuum tube 1650 is then put inside the barrel 1642 of the frame. The inner needle 1643 will penetrate the cover 1651 of the vacuum tube. When the valve 1644 of the frame is located at a "open" position, the hole 1645 will be connected to the hole 1649 in the septum 1648 and the vacuum will be transferred to the lumen 1427 of the sample tube 1422. As a result, the fluid will run through the filter (membrane) and be collected in the vacuum tube. At the same time the cell, cell debris, cell organelle and/or tissue fragments will be held by the filter (membrane). In this way, the cell and/or tissue materials will be separated by a ready-to-use vacuum system. After this separation, sample tube 1422 will be separated from the frame and the hole 1425 will be sealed by a sealing material. Sealing material may comprise a tape, gel material or other materials which can prevent water leakage can be used to seal the any open spaces in the filter. Alternatively, a second plug which contains sealing materials such as petroleum jelly (Vaseline) or sticky tape or others can be used to cover the first plug from the outside. Then the matrix material can be added in the tube and a cell-matrix mixture will be made. After cooling down at lower temperature (4° C.), the mixture can be moved out by either punching out or by a different way, for example, move the plugs out of the tube to let the end of the tube open and pushing the mixture out from the open end by using a plunger from the top to the bottom of the tube. The mixture will be directly placed in the hole of the specifically designed cassette. The collected fluid in the vacuum tube can be used for different tests including pH, chemical, biochemical, immunological, molecular and other studies. Though a vacuum control valve is preferred in this device to control the vacuum achieving and releasing, the device can be designed without the vacuum control valve in order to cut the cost of the manufacture.

In a different setting, sample tube 1522 contains only the non-tapered, reduced diameter bottom region or chamber 1538 with a non-tapered, reduced diameter, cylindrical lumen-sample collecting chamber 1527. Sample tube 1522 can be put inside a tube holder 1660 in a manner that the top of the tube 1528 faces the bottom wall 1661 of the tube holder 1660. The sample collecting chamber 1527 will connect the central lumen 1665 of the nipple 1664 of the tube holder 1660. Then the frame of the device 1641 can be tightly connected to the tube holder 1660 by screwing. Then the vacuum tube 1650 will be put inside the barrel of the frame as described above. A vacuum control valve 1644 will be used to control the vacuum. When the valve is located at a "open" position, the hole 1645 of the valve will connect the hole 1649 of the septum 1648 and the vacuum will be supplied to the sample collecting chamber, the central lumen of the nipple and the needle. When the vacuum valve is at a "close" location, the hole 1645 will be disconnected to the hole 1649 and the vacuum will not be supplied to the sample collecting chamber and the needle. When the needle is inside the target tissue during a procedure of aspiration, the valve can be put in the "open" location and the vacuum provided from the vacuum tube will transferred to the tissue and cells and tissue fragments will be sucked into the sample collecting chamber of the sample tube B through the needle. The cells, cell debris, tissue fragments will be held by the filter (membrane) of the sample tube. Fluid aspirated from the tissue will pass through the filter and collected in the vacuum tube. As a result, the target cells and tissues fragments will be separated from fluid during the procedure of aspiration and will be ready to make a cell block. Once the procedure is done, the vacuum control valve will be placed at a "close" position. The vacuum in the sample tube and the needle will be released. The needle can then be moved out from the tissue without cell and tissue fragments being reflux back through the needle to the target tissue. The device will be placed in a position with the needle facing up. The sample tube holder will be separated from the frame of the device and the sample tube 1522 will be moved out from the device frame. The hole 1525 will be sealed and a cell-matrix mixture will be made as described above.

While the preferred embodiment of the invention utilizes cells obtained by fine needle aspiration, it should be clear to one of skill in the art that cellular material captured by other means could also be utilized to separate cells and tissue fragments from fluid and create a cytoblock. For example, the nipple 1664 of the tube holder 1660 can be connected to a catheter or other tubes, instead of a needle. In this way, the device can be used to collect cells and tissue fragments from other procedures such as endoscopy, including but not limited to arthroscopy, bronchoscopy, colonoscopy, colposcopy, cystoscopy, ERCP (endoscopic retrograde cholangio-pancreatography), EGD (esophogealgastroduodensoscopy), endoscopic biopsy, gastroscopy, laparoscopy, laryngoscopy, proctoscopy and thoracoscopy. Cells could also be obtained from lavage procedures, including but not limited to bronchoalveolar, breast ductal, nasal, pleural, peritoneal, gastrointestinal, arthroscopic, and urinary bladder lavages. It is also contemplated that cells could be collected from catheters such as those used in infusion, cardiovascular, rental, bladder, urethral, hemodynamic monitoring, neurological, and other procedures which would be obvious to one of skill in the art.

Figure 45:
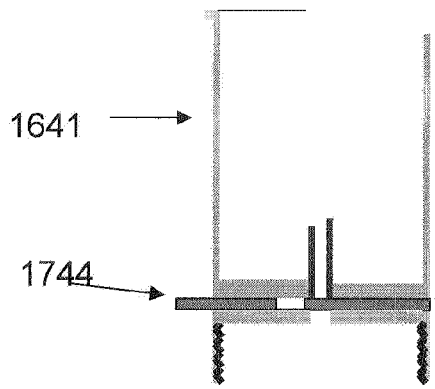
Figure 45:
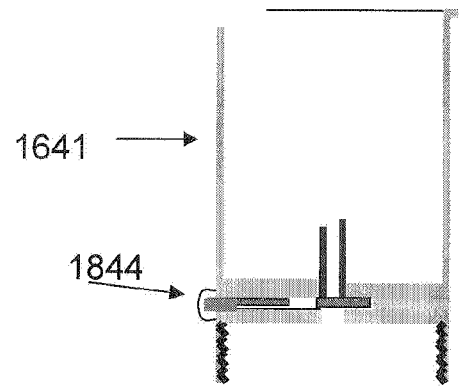
Figure 54:
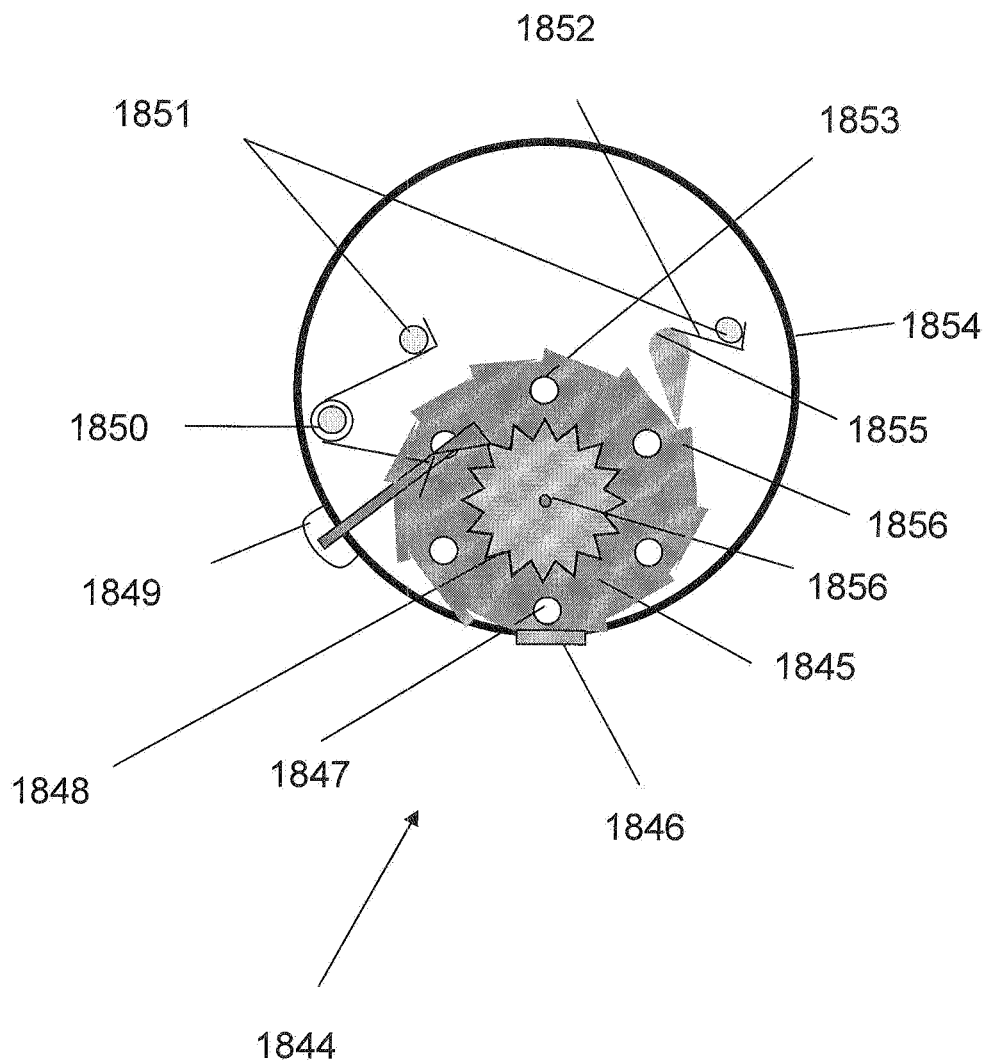

The vacuum control valve 1644 can be designed in different forms and located in different locations of the device. FIGS. 45(A) and 45(B) illustrate two examples of these different valves: Pushing valve 1744 and rotating valve 1844. FIG. 54 illustrates a rotating valve comprising of different components. The vacuum position indication window 1846 is designed to demonstrate the "opening" and "closing" of the vacuum by showing different colors. For example, a green color indicates an "open" of the vacuum and a red color indicates a "close" of the vacuum. In the presenting drawings, the valve 1644 is located in the septum 1648 and is more close to the end which connects the sample tubes. Alternatively, the valve can be located at different locations of the frame of device. The valve 1844 is composed of different parts including a vacuum position indication window 1846, a hole 1847, gear wheel 1848, soft plastic cover 1849, spring 1850, levels for spring 1851, spring 1852, hole to inner needle 1853, barrel 1854, step stopper 1855, steps 1856, axis 1856.

A vacuum indicator will be put into the system, either in the vacuum tube or associated with the vacuum valve. This vacuum indicator may reflect the real vacuum status of the vacuum tube or/and the sample collecting tubes. This indicator may be designed based on different mechanisms such as color change, volume change of a ball shape structure, electronic signal or/and transferred digital signal and other possible forms. The vacuum indicator is an important part of the device.

Figure 46:
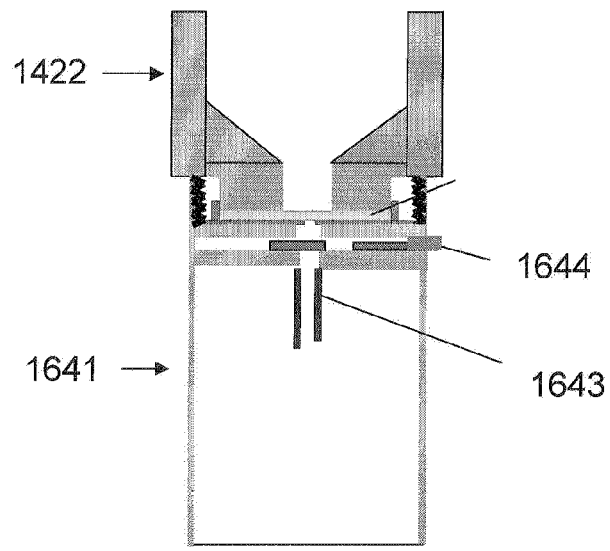

FIG. 46 illustrates the connection of sample tube 1422 to the frame 1641. The tube 1422 can be tightly connected to the device frame 1641 by a screw system 1426 and 1647. The plug 1424 can be tightly attached to one side of the septum 1648 of the frame 1641. The hole 1425 in the plug 1424 can match and connect to the hole 1649 in the septum 1648 to form one channel.

Figure 47:
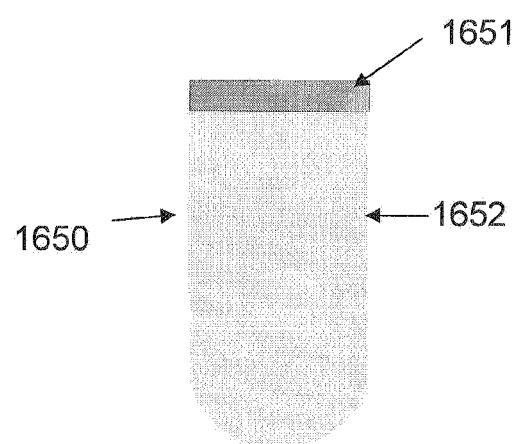

FIG. 47 illustrates a vacuum tube 1650 which has a rubbery cover 1651 and a tube 1652 which contains vacuum.

Figure 48:
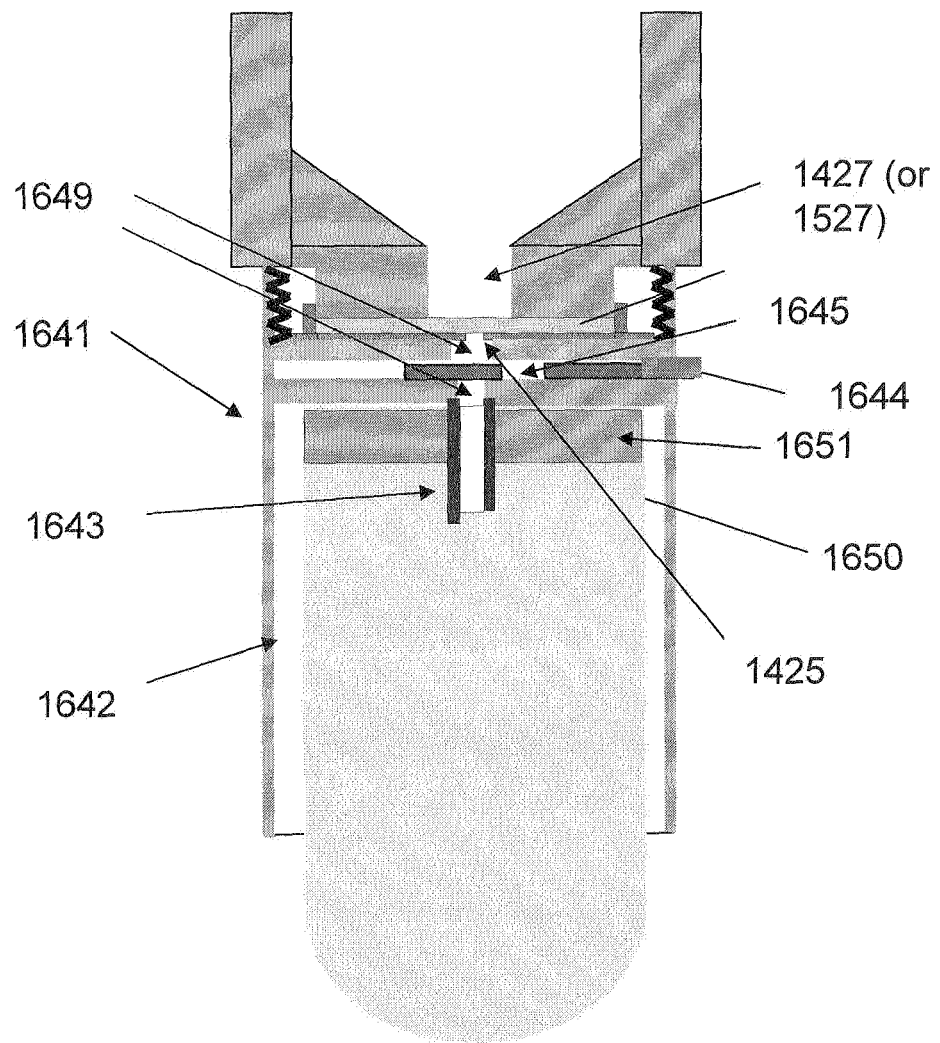

FIG. 48 illustrates a connection between the vacuum tube 1650 and the frame 1641. The vacuum tube 1650 can be put into the barrel 1642 of the frame 1641. The inner needle 1643 will penetrate the cover 1651 of the vacuum tube. When the valve 1644 is moved to a position to allow its hole 1645 connect to the holes in the septum, the vacuum will be transferred from the tube 1650 through the inner needle 1643, the hole 1649 in the septum, the hole 1645 in the valve and the hole 1425 in sample tube 1422 or 1525 in the sample tube 1522, the membrane 1423 and finally to the channel 1427 or 1527 of the sample tubes.

Figure 49:
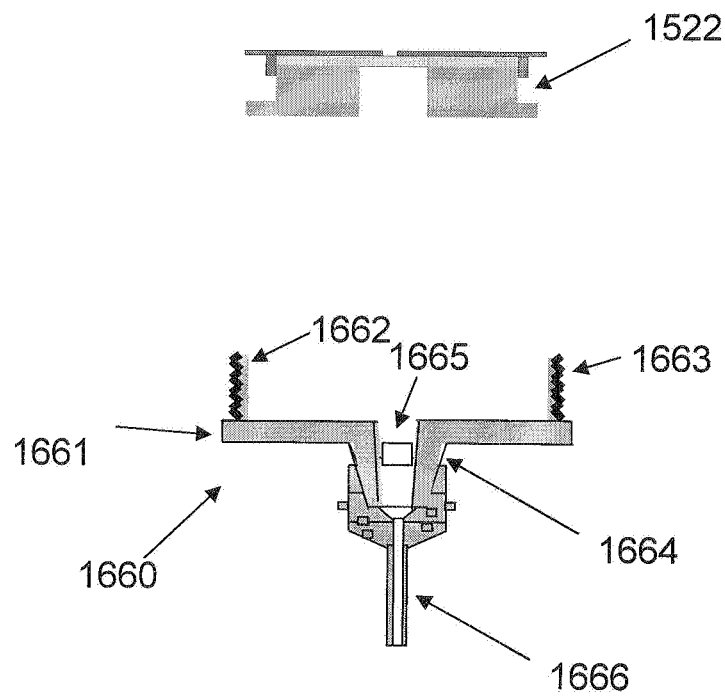

FIG. 49 illustrates a tube holder 1660 which has a bottom wall 1661, a side wall 1662, and a screw 1663 at the outer surface of the side wall, and a nipple 1664. The bottom wall 1661 is round and has a flat surface. The nipple 1664 is located in the center of the bottom wall and has a central channel 1665. The nipple can be used to connect the needle 1666. The side wall 1663 is round in shape and the outside screw can be used to connect the frame 1641. The side wall and bottom wall together form a chamber which can hold the sample tube B 1522.

Figure 55C:
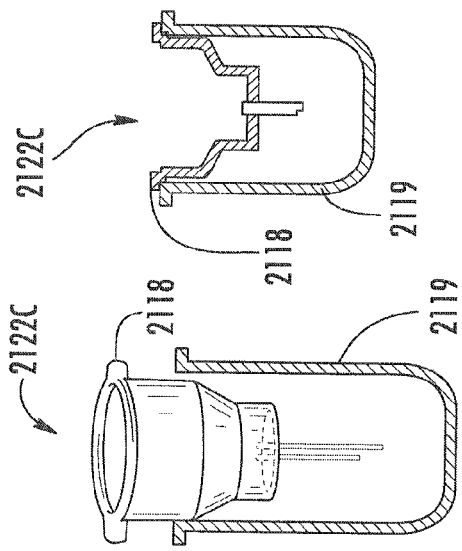
Figure 55B:
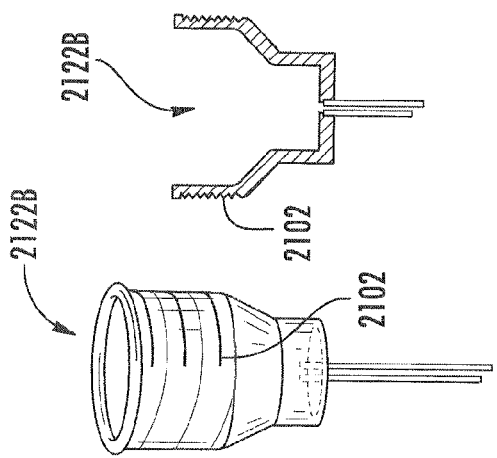
Figure 55A:
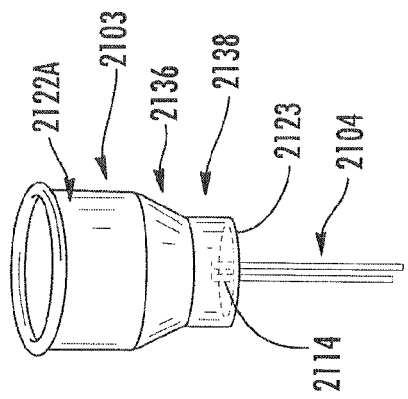

FIGS. 55A-C illustrate a collecting tube 2122 (2122 A, B and C). In FIG. 55A, tube 2122 A is a modified embodiment of tube 22 and has a tapered region 2136 and a non-tapered, reduced diameter bottom region or chamber 2138 with a flat plane floor 2123. FIG. 55A illustrates the tube 2122 A with a needle shaft 2104 penetrating through the flat floor 2123 and protruding into the inner space of the chamber 2138 with a upper portion of the shaft 2114 located above the floor. Briefly, this upper portion 2114 of the shaft 2104 has two specific functions: 1) prevent the reflux of collected specimens back through the shaft; 2) make a dot marker on the bottom surface of a cell-matrix mixture block which can be used as an orientation marker in the embedding process. Basically, the cell matrix mixture is made and maintained in a cylindrical shape and the cells are located at the area of bottom surface and this bottom surface needs to be embedded on the cut surface of the final paraffin block. It is easy to confuse the top and bottom surfaces during the process because they look similar to each other. With the presence of upper portion 2114, the 2114 will occupies a small space in the bottom portion of the mixture G and a small hole (dot marker) will be generated when the mixture G is moved out of the tube and this small hole will be worked as a marker of the bottom surface. The small hole itself can be used as a orientation marker. The bottom surface can also be gently inked with a specific ink and this hole will catch the ink and highlight the bottom surface.

In FIG. 55B, tube 2122B is a different embodiment of tube 2122 A. Tube 2122B has a screw 2102 on the outer surface of the upper portion of the tube 2103. The screwing surface will help the tube to connect to a specifically designed syringe or other vacuum system by the screw.

In FIG. 55C, tube 2122C is a different embodiment of tube 2122A. Tube 2122C has a "ear" or "shoulder" protruding portion 2118 on the top of the tube. The portion 2118 works as a part of the lure lock to connect to a specifically designed syringe. A supporting tube 2119 can also be added to the system. This tube has two functions: 1) support the tube 2122 A, B, C when the tube is centrifuged to separate the supernatant and the cells; 2) shelter the needle and collect the possibly leaked material from the tube.

FIG. 56 illustrates specifically designed frame of vacuum device 2141. The frame 2141 has a barrel 2142, a piston 2143 and a connecting portion 2146 and a screw 2147 on the inner surface of the connecting portion 2146. In FIG. 56A, a septa 2148 is located to separate the barrel and the connecting portion and there is an opening 2149 at the center of the septa 2148. In a different embodiment, a piece of cushion 2130 can be placed on the lower surface of the septa and this cushion will directly contact with a upper edge of the tube 2122 (A, B, C) to better seal the connecting point between the septa and the upper edge of the tube. FIG. 56 B illustrates another embodiment of the vacuum device. The septa is replaced by a nipple 2131 which combined with the connection portion 2146 and a screw 2147 to form a lure lock which then can be connected to tube 2122 through the portion 2118. The diameter of the nipple will be fit the size of the tube 2122C. In another embodiment, a filter membrane 2132 can be put on the opening of the nipple to avoid the collected specimens leaking to the barrel of the vacuum device through the opening 2149 A of the nipple.

FIG. 57 illustrates different embodiments of tube 22. FIG. 57 A illustrates tube 2222 with a frame 2422 and an open bottom 2423.

FIG. 57B illustrates a flat plane 2223. The frame 2422 and the flat plane 2223 can be mounted together by different methods to form a tube 2222A as illustrated in FIG. 57D.

FIG. 57C illustrates a plug 2225 which is considered as a different embodiment of plane 2223. Plug 2225 can be mounted to the frame 2422 B to form a tube 2222 B with a flat bottom surface by pushing the tube frame into the plug. A cushion 2230 can be placed on the inner surface of the plug to seal the connection between the frame and the plug more efficiently.

FIG. 57F illustrates a different embodiment of the connection between the frame 2422 C and the plug 2226 by a screw type connection.

FIG. 57G illustrates a different embodiment of the flat plane 2223. In this embodiment, a needle shaft 2104 penetrates the flat plane 2223 with its upper portion 2014 located above the plane.

FIG. 57H illustrates a different embodiment of the upper portion 2014 of the shaft 2104. In this embodiment, the upper portion of the shaft has a curve 2015. The upper opening of the shaft is located above the plane 2223 and this location will avoid the re-flux of collected specimen through the shaft. The curve 2015 will help to guide the collected specimen stored along a side wall of the tube to avoid spreading during the aspiration. The needle shaft can be located at different areas of the flat plane including a central or an eccentric location or at the edge.

FIG. 58 illustrates different embodiments of the connection between the chamber 38 and the plug 2225. FIGS. A, B, C and D illustrate different embodiments of chamber wall 2238 A, 2238 B, 2238 C, and 2238 D with matched plugs 2225A, 2225 B, 2225 C and 2225 D, respectively. The chamber wall 2238 can also be formed of two parts with a joint formed across the whole chamber. As illustrated in FIG. 57A.

FIG. 59 illustrates different embodiments of the tube 2222 with its chamber mounted to a plug which carry a needle.

FIG. 60 illustrates a different embodiment of the system. In this embodiment, only the chamber portion 38 of the tube 22 will be employed.

FIG. 60A is a copy of the FIG. 42 in the application U.S. 60/846,036. And it was described as the follows:

FIG. 60A illustrates a specimen collector 2002. Collector 2002 is designed to contain three parts including a metal shaft 2004 with a central lumen 2006, a sharp bevel 2008 and a hub

2010, as in a needle. The most important difference between this novel collector and a conventional needle is that the hub of the collector is designed in a specific size and shape to enable the hub itself function as a collector of specimen, instead of functioning only as a connector between the syringe and the shaft of a syringe in a conventional needle.

The example embodiment of the hub is in a cylindrical shape, though it could also be in other shapes. The bottom 2016 of the hub should be flat and in a round or other shape. The inner space 2012 of the hub should be at least 4 mm in diameter (The hub of a conventional needle has an inner space with a diameter up to 4 mm). The length of the hub is variable (2 to 25 mm) depending on specific requirement of different procedures and target organs. The upper portion of the metal shaft 2014 can be located in a manner that it penetrates the bottom of the hub 2016 and protrudes into the inner space 2012 of the hub with a variable length of the protrusion (0 to 20 mm). The shaft 2004 and its upper portion 2014 can be located at variable location of the bottom 2016 of the hub including a central location or an edge, or eccentric location. The upper portion 2014 of the shaft can be either straight or with a curve to direct the collected material to a sidewall of the hub. The hub may has a "ear" or a "shoulder" 2018 which may works as a part of a lure lock to connect the collector 2002 to a vacuum system such as a syringe. The collector can also be connected to a vacuum system by gel, glue or other chemicals. The collector will be separated from the vacuum system by using a physical force or other methods, after the FNA procedure."

FIG. 60B illustrates the curved upper portion 2015 of the needle shaft. The upper portion of the needle may be curved to guide the collected cells or tissue fragments toward a side of the chamber of the tube. This covered portion will prevent the cells from running up into the barrel of the vacuum device. The curved portion 2015 could be a part of the needle shaft. Alternatively it could be extended out from one portion of the proximal end of the needle shaft as an "umbrella" or "cover". Alternatively, the "umbrella" or "cover" structure can also be extended up from the floor adjacent to the proximal opening of the needle.

FIGS. 60C and D illustrate examples of different embodiments of the chamber using the same principle illustrated in FIGS. 57, 58 and 59. FIG. 60D illustrates an embodiment where metal shaft or needle 2004 has an upper end adjacent to the floor or bottom 2026 and where a cover 2027 extends across and over the central axis of lumen 2006. As a result, cells and/or tissue drawn through lumen 2006 is directed in a sideways direction to reduce the potential for tissue loss caused by such cells or tissues being drawn further up into the barrel of a syringe. In one embodiment, the cover 2027 is formed as part of the needle 2004. In another embodiment, the cover 2027 is formed as part of the floor or bottom 2026 (shown in FIG. 60D).

FIG. 61 illustrates a syringe type vacuum system 2032. The vacuum system 2032 contains a barrel 2038, a plunger 2040 and lure lock 2036 and a nipple 2034. The diameters of the nipple and the lure lock should be variable to fit the hub 2002. In addition, a filter membrane 2035 may be placed at the lower opening of the nipple to avoid the collected specimens leaking to the barrel of the vacuum device through the opening of the nipple.

FIG. 62 illustrates a different embodiment of "Modified tube for vacuum methods" as illustrated in FIGS. 20 to 32. In this embodiment, the plug 2625 in FIG. 62 B contains a flat bottom 2627 with central opening 2649. A filter membrane 2630 is placed on the inner bottom surface.

FIG. 62C illustrates a tube 2622A formed by mounting the plug 2625 with the tube 2622.

FIG. 62D illustrates a different embodiment of vacuum device 1029 as described in FIGS. 29 and 31. In this embodiment, a vacuum device 2629 has a barrel 2636, a bottom 2631, with extended stand 2632. On the upper inner surface of the barrel, there is a screw 2633. On a side wall, there is an opening plug 2634 with a "ear" or "shoulder" 2635 which can connect to a syringe by a lure lock.

FIG. 62E illustrates a connection between the tube 2622A and the vacuum device 2629 in a fashion of forming a screw 2636.

FIG. 62F illustrates a different embodiment of the tube 2622. In this embodiment, the connection between the frame of the tube and the plug is in a screw type.

FIG. 63 illustrates different embodiments of vacuum valves which are illustrated in FIG. 45A and FIG. 45B. In these embodiments, there is no inner needle.

Figure 50:
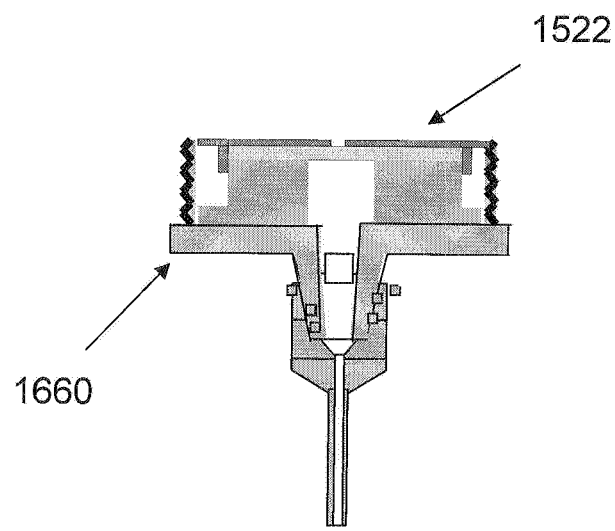
Figure 51:
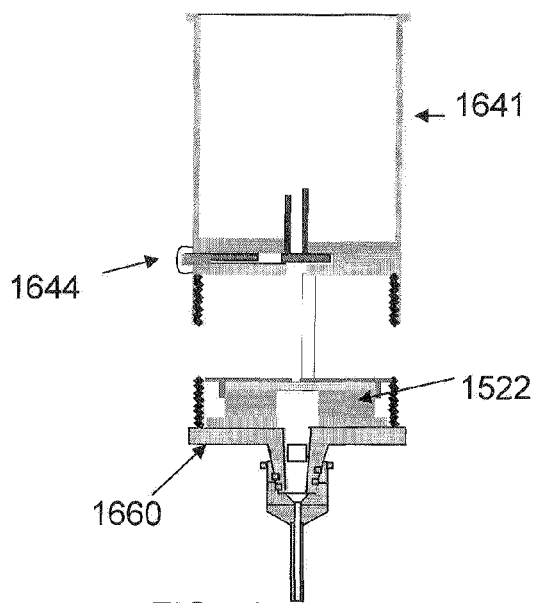
Figure 52:
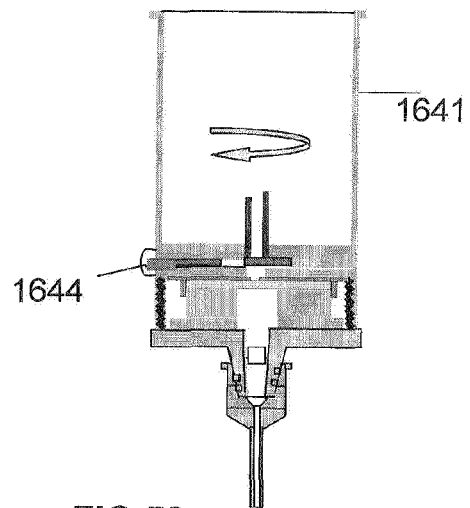
Figure 53:
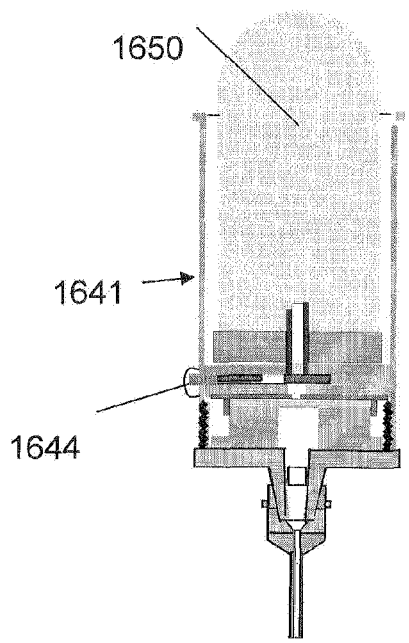

FIG. 64 illustrates a different embodiment of sample tube B 1522 illustrated in FIG. 43 and a tube holder 1660 illustrated in FIGS. 49 and 50. In this embodiment, the sample tube 1522A is same as 1522. There is no nipple present in the tube holder 1660A. Instead, a needle shaft 1604A penetrates through the flat bottom floor 1661 A and with the upper portion 1614A protruding into the inner space 1527A of the sample tube 1522 A.

Figure 8:
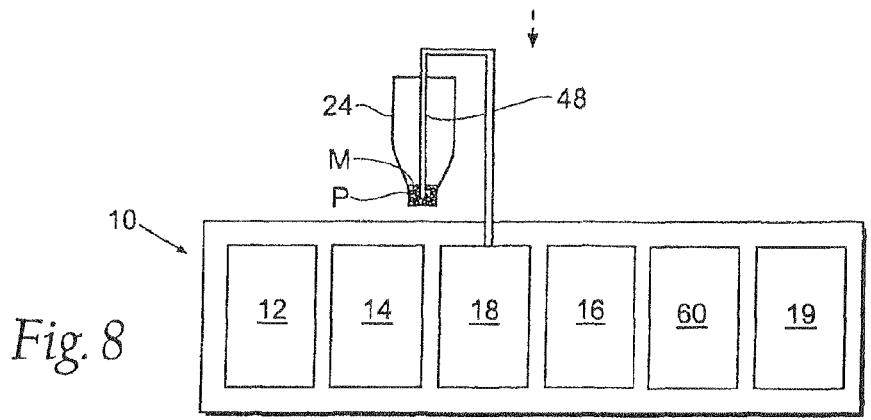
FIG. 8 is a schematic block diagram illustrating the mixing of the matrix material and the cellular pellet using a mixing probe.
Figure 65:
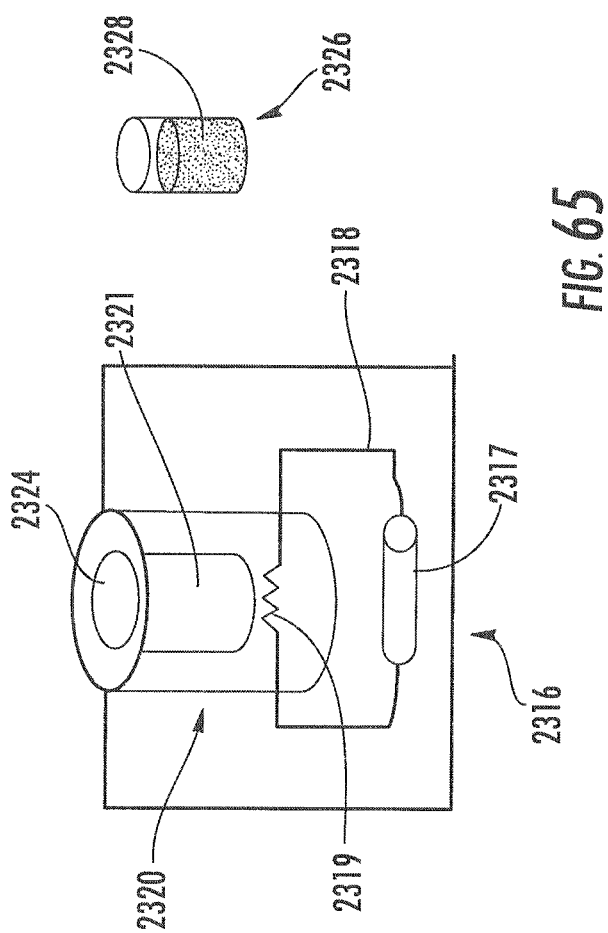

FIG. 65 illustrates a portable embodiment of incubation carrier or chamber 16 as illustrated in FIG. 8. In this embodiment, the inner incubation chamber 2316 is battery powered and is portable. It contains a battery 2317, an electric resistance 2319 which is connected to the battery by a connecting wire 2318, a heating chamber 2320 with an inner space 2324. A matrix container 2326 containing matrix 2328 can be placed inside the inner space 2324 of the heating chamber 2320. It also contains a switch (not show in the picture) to adjust the temperature of the chamber. The temperature can be adjusted from 0 to 100 degrees C.

FIG. 66 illustrates a specially designed forceps used to transfer the relatively solid cell-matrix mixture G from the tubes to a specifically designed cassette as illustrated in FIGS. 8 to 10. In this embodiment, as illustrated in FIG. 66 A, the forceps 80 has two arms 85 which joint together by a joint 84. The lower portion of the forceps 81 has semi-annular shape. There are spaces between the two arms. The lower portion 81 of the two arms can form a cylindrical shape by pushing the two arms toward each other. The diameter of the cylindrical space between the two arms should match with the diameter of chambers 38, 1522, 2138, 2238, 2012, 1527, and 1527 A.

Figures 66A, 66B, 66C:
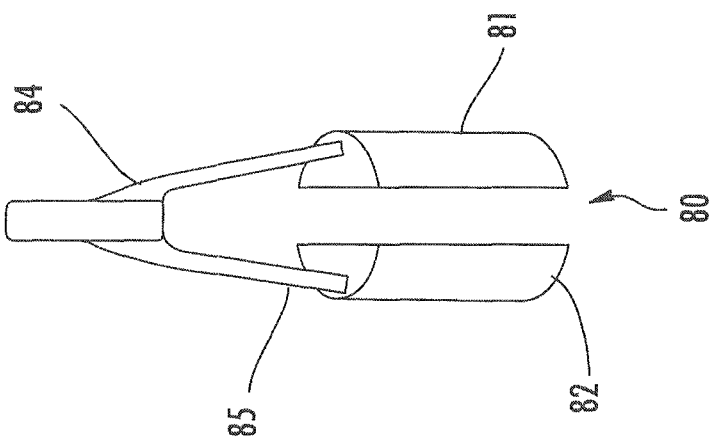
FIG. 66 illustrates a transfer forceps according to an example embodiment.

FIG. 66B illustrates a bottom view of the lower portion of the forceps 80. The bottom 82 should be flat.

FIG. 66C illustrates a inner face of the lower portion of the arms. There are some teeth-like structures 83 on the inner face to help holding the mixture G during the transferring process.

Figure 11B:
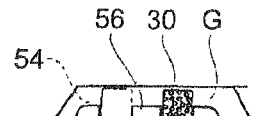
FIG. 11B is a schematic illustrating an alternative embodiment of a tissue cassette in which the chamber is removable.

FIG. 67 illustrates different embodiment of specifically designed cassette 30 as illustrated in FIG. 11A and FIG. 11B. In this embodiment, cassette 30A has slits or openings through its floor to permit passage of fluids therethrough and further contains a sponge plate 31A with a open spaced chamber 54A. The chamber 54A should have a shape and size matched with the mixture G to maintain the shape and orientation of G. In another embodiment, there may be a web or filter paper being placed under or/and above the sponge plate to cover the sponge chamber in order to prevent possible loss of cells in the mixture G during the process. In other embodiments, plate 31 may be integrally formed as a single unitary body with a remainder of cassette 30.

FIG. 67C illustrates a different embodiment of the sponge plate 31B which contains multiple chambers 54 B and an orientation marker 32. The marker can be a defect of the sponge plate (for example a defect at one corner), an inked area, or specific labeling.

FIG. 68 illustrates a different embodiment of a transfer tube 26, 126, 226, and 326 as illustrated in FIGS. 10, 11A, 19A, 19B and 19C, respectively. In this embodiment, the transfer tube 126A contains a tamp 128A with central opened lumen 130A with or without a structure 129A at the bottom of tamp. A vacuum can be employed through the central lumen to the bottom of tamp and the upper surface the mixture G to help holding the mixture G during the transferring process.

FIG. 69 illustrates another embodiment of the transfer tube of 126. In this embodiment, there is a thin layer, flexible narrow plate like structure 132 is placed along the wall of the tube 126 B with a handle 131 which can move along the tube. After punching the mixture G into the tube 128B, the handle 131 will be moved down along the tube wall. The lower end of the structure 132 will encounter with the bottom surface of the chamber 38 and be bended toward the center of the chamber along the bottom surface of the chamber 38. This bended portion 133 of the structure will help to move the mixture G from the chamber and be transferred to a cassette. The structure 132 can be designed as a single plate as illustrated in FIG. 69. It can also be multiple and located toward to different directions. It may be located inside or outside the transfer tube or even inside the wall of the tube.

FIG. 70 illustrates a different embodiment of tube 22. FIG. 70A illustrates a modified tube 2722 contains a barrel 2701, a tapered region 2736 and a non-tapered, reduced diameter bottom region or chamber 2738, a flat floor 2725. In addition, a needle shaft 2704 penetrates the flat floor 2725 and with or without the upper portion 2714 protruding into the inner space 2711 of the chamber 2738. The distance between the upper opening of the shaft and the inner surface of the floor 2725 is variable (0-1.5 cm) depending on different situations. The upper portion 2714 could be either straight or curved as described above. In addition, a piston 2705 is also a part of the embodiment. The piston has a central column 2706 with a tapered region 2707 at the lower portion of the column and a flat bottom 2708. This piston could be in different shape and made of different materials, though the embodiment 2705 is preferred. The piston is in a size and shape fitting the inner space 2710 of the barrel 2730. In the practice of FNA, needle shaft is put inside the target tissue, the piston is pulled out from the inner space of the barrel and a vacuum is generated in the inner space of the barrel and transferred to the target tissue through the lumen of the needle shaft. The vacuum will suck the target cells and tissue into the inner space 2711 of the chamber 2738.

FIG. 70B illustrates another embodiment of the tube 2722. In this embodiment, the barrel 2730 is composed of upper 2701 and lower 2702 portions. The two portions are mounted together by a joint 2703. The joint 2703 can be located at different location along the barrel; even can be down across the tapered regions 2736 and/or non-tapered chamber 2738. The inner surface of the barrel including the joint area should be smooth. The methods used to form the joint including 1) direct connection of the two portions by gel, glue, ultrasound, UV light and other methods; After finishing the sample collection, the two portions can be separated from each other by a pushing force targeted on the joint area or other methods; 2) different methods to form a joint based on the principles described in FIGS. 57, 58, 59 and 60.

Figure 70D:
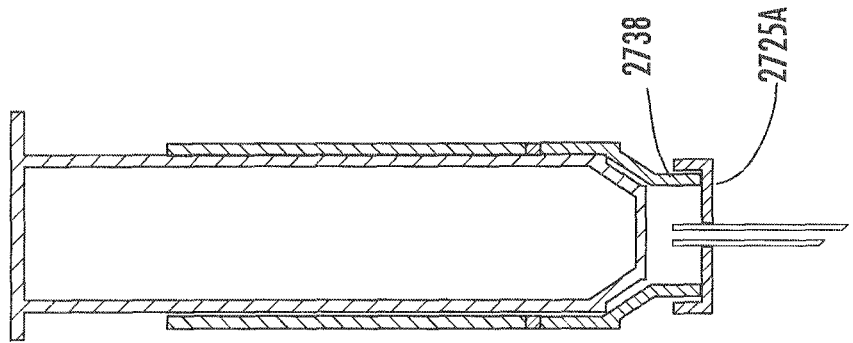
Figure 70C:
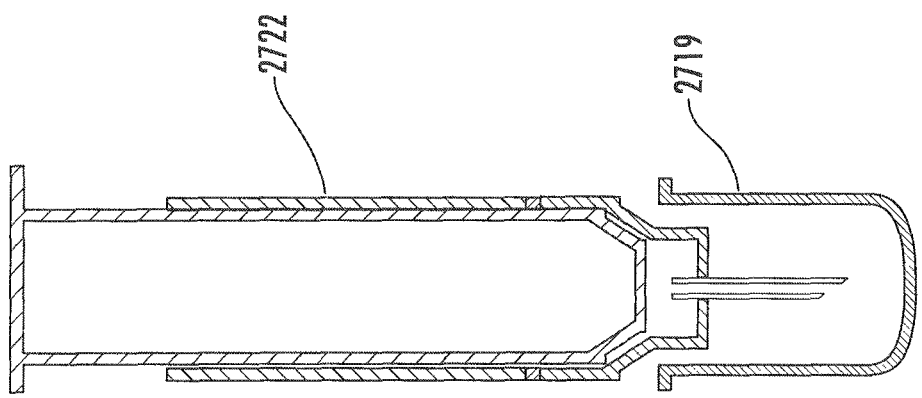

FIG. 70C illustrates a embodiment of the modified tube 2722. A support tube 2719 is also added into the device.

FIG. 70D illustrates a different embodiment of tube 2722. In this embodiment, the plug 2725 A is employed to replace the flat floor 2725. Different methods of connecting the plug 2725A to the chamber 2738, based on the principles described in FIGS. 57, 58, 59 and 60, may be employed.

The tube 2722 has three specific functions. First, the tube 2722 works as a fine needle aspiration device. In the practice of FNA, needle shaft 2704 is put inside the target tissue, the piston 2705 is pulled out from the inner space 2710 of the barrel and a vacuum is generated in the inner space of the barrel and transferred to the target tissue through the lumen of the needle shaft. The vacuum will suck the target cells and tissue into the inner space 2711 of the chamber 2738.

Second, the tube 2722 works as a specimen collector to store the collected material. The collected materials run through the shaft 2704 and directly get into the inner space 2710 of the tube. This process eliminates any possible loss of the collected material during their journey from a shaft to the hub of conventional needle and to the connecting joint between the hub and a collector and a possible nipple of the collector and finally reaches the collecting space of a collector such as the barrel of a syringe.

Third, the tube 2722 works as a device where the collected materials may be directly used to make a cell block. Collected materials from a FNA procedure using this device will be directly stored in the inner space 2710 and ideally in the inner space 2711 of the chamber 2738. After finishing FNA procedure, the needle shaft will be amputated by a specific tool similar to a vice, pincer or pliers. In this amputation process, the distal end of the shaft will be de-sharpened and the lumen of the shaft will be sealed either by a direct force which pushes the wall of the shaft close to each other and finally seal the lumen, or by filling the lumen with special materials such as wax, gel, tape, or rubber or others. The supporting tube 2719 will be used to cover the bottom portion of the tube 2722. If the collected materials is less than 300 micro liter (ul), a adequate amount of matrix will be added into the inner space 2711 to make a cell-matrix mixture G, the tube 2722 will be put at a lower temperature such as on ice or in a cooler for a few minutes and the mixture G will be relatively hardened. At this moment, the G will be moved out from the inner space 2711 of the chamber and be transferred to a specific cassette as described in FIGS. 10, 11 and 67 by a specific transfer tube as described in FIGS. 10, 11, 19 (A, B, C) and 68 or forceps 80 as described in FIG. 66. If the collected specimen has a large volume (>400 ul), the tube will be put into a special centrifuge to spin down the cells to the flat floor of the chamber 2738, the supernatant will be moved out by different methods including a pipette or a portable version of a vacuum device 14 as described in FIGS. 4 and 5. The remaining cell pellet will be used to make a cell matrix mixture G using the method as described above.

In another embodiment as described in FIG. 70B, after collecting the specimen, the lower portion 2702 of the barrel 2730 will be separated from the upper portion 2701 from the joint 2703, and the lower portion will be used for the cell block preparation as described above.

In another embodiment as described in FIG. 70D, after making a mixture G, instead of transferring G from the chamber by a transfer tube or forceps, the plug 2725 A can separated from the chamber 2738, and the mixture G will be put into a chamber 54A of a specifically designed cassette 30 A as described in FIG. 67 directly by pushing the G down through the lower opening of the chamber using a tamp.

This device can also be used in bone marrow aspiration. In current bone marrow aspiration procedure, a specific bone marrow biopsy device (such as LEE-LOK manufactured for LEE Medical, LTD.) with a long and wide needle (11 gauge and 5½ inch) is used to penetrate the skin, subcutaneous soft tissue and bone. During this penetrating process, a tamp is located inside the lumen of the needle to avoid a blockage of the lumen by the fragments of skin soft tissue or bone. After penetrating through the bone and reaching into the bone marrow, the tamp is moved out and the lumen of the needle will be opened, then a syringe is used to aspirate bone marrow from the lumen. And the collected bone marrow will be used to make glass smears and cell block. There are two steps to make a cell block of bone marrow in the current practice: aspiration by a syringe and transfer the collected bone marrow to a device to make the cell block. In one embodiment of our tube 2722, the needle shaft of the tube will be designed in an adequate size and length to fit and match with the lumen of the bone marrow biopsy needle. And bone marrow can be directly aspirated into the inner space 2711 of the chamber of the tube 2722 and a cell block can be directly made as described above.

The systems and methods described above enable a physician, for the first time, to perform a FNA and make a cell block using same device at the same location in a very short time. This system has a few notable advantages over the traditional FNA and cell blocking procedure: 1) it maximally utilizes the collected material from a FNA procedure for a diagnostic purpose, 2) it takes much shorter time and much less steps to make a cell block and shorten the turnaround time in practice, 3) tt saves the time and labors of the technologists in making the cell block using traditional methods, 4) the size, shape and thickness of the cell block can be controlled and the limited available materials can be used efficiently to make enough sections for IHC or other special studies if required.

FIG. 71 illustrates another embodiment of tube 2722. In this embodiment, the barrel 2701A of the tube 2722A does not have a tapered region and a non-tapered, reduced diameter chamber. The floor 2725A is either flat or slightly curved. A upper portion 2714A of A needle shaft 2704A is at the same level of the floor 2725A and does not protrude into the inner space of the barrel. The bottom surface 2708A of the piston 2705 is in a shape which exactly matches the inner surface of the floor 2725A. In this case, when the piston is put inside the barrel, the bottom surface of the piston will completely attached on the inner surface of the floor 2725A and there is no space present between the two surfaces.

The above tube embodiment 2722A has a several notable significances over a conventional syringe with an attached needle.

First, a metal needle shaft is directly extends to the bottom of a floor of a barrel with the inner lumen directly extends to the inner space of the barrel and there is of a needle and the inner space of the barrel. This setting may maximally reduce any possible liquid leakage and retaining material in these additional connections and joints. When using this device to deliver a liquid medicine or chemical, it will be more accurate to deliver a right dosage than a conventional syringe. Such an accurately delivery may be critical in some clinical scenario, for example, if the delivered medicine has a strong effects and side effects, or it is toxic, or it is very rare and very expensive.

Secondly, manufacture of this device may be much simpler and cheaper. Thirdly, it may be easier and friendlier to use since it is ready to be used, instead of opening a syringe and a needle separately and then assemble them together to use.

Fourthly, as a disposable device, it can be designed to have two functions: 1) it is filled with a specific volume of a specific liquid medicine or chemical and the distal opening of the shaft is covered using a specific method and it is ready to be used, in this way, it works as a specific container of the specific medicine or chemical; 2) it works as a syringe to directly deliver the pre-filled medicine or the chemical to its target, instead of assembling a syringe with a needle and suck the medicine into the syringe first before deliver the medicine into the target.

Although the present disclosure has been described with reference to example embodiments, workers skilled in the art will recognize that changes may be made in form and detail without departing from the spirit and scope of the disclosed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments.

What is claimed is:

1. A method of preparing a cytoblock comprising:
   a. preparing a cell pellet in a centrifuge tube having a flattened floor;
   b. combining the prepared cell pellet with a matrix material in the centrifuge to form a cell mixture;
   c. transferring the cell mixture from the centrifuge tube into a tissue cassette having at least one integrally formed chamber that is compatible in size and shape with the bottom region of the centrifuge tube having the flattened floor and processing the mixture; and
   d. embedding the processed cell mixture in an embedding block.

2. The method of claim 1, wherein the preparing further comprises:
   a. depositing cell material in the centrifuge tube;
   b. adding a predetermined amount of fixative to the centrifuge tube;
   c. placing the centrifuge tube in a centrifuge device to create the cell pellet and supernatant; and
   d. removing the supernatant from the centrifuge tube.

3. The method of claim 1, wherein the centrifuge tube further comprises a tapered region and a non-tapered, reduced diameter bottom region.

4. The method of claim 1, wherein the tissue cassette includes a removable insert having at least one integrally formed chamber.

5. The method of claim 1, wherein the preparing further comprises depositing cell material in a centrifuge tube containing a predetermined amount of fixative, placing the centrifuge tube in a centrifuge device to create the cell pellet and supernatant; and removing the supernatant from said centrifuge tube.

6. The method of claim 5, wherein the cell material is obtained by fine needle aspiration.

7. The method of claim 5, wherein the cell material is obtained by endoscopy.

8. The method of claim 5, wherein the cell material is obtained by lavage.

9. The method of claim 5, wherein the cell material is obtained by a catheter.

10. The method of claim 1 wherein the combining further comprises:
    a. providing a matrix container containing the matrix material, the matrix container having the form of a syringe;
    b. heating the matrix container to liquefy the matrix material;

c. depositing a predetermined amount of liquefied matrix material into the centrifuge tube;
d. mixing the cell pellet and the matrix material to create a suspension; and
e. cooling the centrifuge tube to solidify the matrix material and create a cell mixture.

11. The method of claim 1, wherein the embedding further comprises:
   a. transferring at least a portion of the cell mixture from the tissue cassette to an embedding block made of wax and formed with at least one hole therein to receive the at least a portion of the cell mixture;
   b. placing an embedding tray over the embedding block and inverting the embedding tray and embedding block;
   c. warming the embedding tray and embedding block to at least partially melt the embedding block and embed the cell mixture in the embedding block; and
   d. cooling the embedding tray and embedding block to solidify the embedding block.

12. The method of claim 1, wherein the embedding further comprises:
   a. transferring at least a portion of the cell mixture from the tissue cassette to an embedding tray, the embedding tray being provided with a partitioned insert formed with at least one partition therein to receive the at least a portion of the cell mixture;
   b. depositing a predetermined amount of embedding material into the embedding tray to embed the cell mixture into an embedding block, said embedding material being heated to liquefy the embedding material; and
   c. cooling the embedding tray to solidify the embedding block.

13. The method of claim 1, wherein the embedding further comprises:
   a. transferring at least a portion of the cell mixture from the tissue cassette to an embedding tray, the embedding tray provided with liquefied embedding material therein and a portioned insert formed with at least one partition therein to receive the at least a portion of the cell mixture; and
   b. cooling the embedding tray to create a solidified embedded block.

14. The method of claim 1, wherein the tissue cassette includes a fixed insert having at least one integrally formed chamber.

* * * * *